(12) United States Patent
Nields et al.

(10) Patent No.: US 7,496,398 B2
(45) Date of Patent: *Feb. 24, 2009

(54) SPATIALLY CORRELATED X-RAY AND ULTRASOUND MAMMOGRAPHIC IMAGING SYSTEMS AND METHOD

(75) Inventors: Morgan W. Nields, Englewood, CO (US); John Connor, Elizabeth, CO (US); Curtis Daly, Denver, CO (US)

(73) Assignee: Hologic Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/260,719

(22) Filed: Sep. 27, 2002

(65) Prior Publication Data

US 2003/0073895 A1    Apr. 17, 2003

Related U.S. Application Data

(60) Division of application No. 09/449,267, filed on Nov. 24, 1999, now Pat. No. 6,459,925, and a continuation-in-part of application No. 09/111,094, filed on Jul. 6, 1998, now Pat. No. 6,102,866, which is a continuation-in-part of application No. 08/730,107, filed on Oct. 15, 1996, now Pat. No. 5,776,062.

(60) Provisional application No. 60/109,881, filed on Nov. 25, 1998.

(51) Int. Cl.
    *A61B 6/02* (2006.01)
(52) U.S. Cl. .................. 600/427; 600/439; 600/461; 378/37; 378/208; 128/915; 128/916
(58) Field of Classification Search .............. 600/439, 600/445, 446, 459, 407, 427, 429, 437, 440, 600/443, 461; 606/130; 378/37; 37/37, 37/208, 209; 128/915, 916
See application file for complete search history.

(56) References Cited

U.S. PATENT DOCUMENTS

| 2,707,662 | A | 5/1955  | Goldfield et al. ............. 311/6 |
|-----------|---|---------|--------------------------------------|
| 3,165,630 | A | 1/1965  | Bielat et al. ................. 250/58 |
| 3,963,933 | A | 6/1976  | Henkes, Jr. ................ 250/456 |
| 3,973,126 | A | 8/1976  | Redington et al. .......... 250/444 |
| 4,051,380 | A | 9/1977  | Lasky ........................ 250/451 |
| 4,099,880 | A | 7/1978  | Kano ......................... 356/164 |
| 4,249,539 | A | 2/1981  | Vilkomerson et al. ....... 128/660 |
| 4,341,120 | A | 7/1982  | Anderson .................... 73/618 |
| 4,346,717 | A | 8/1982  | Haerten ..................... 128/660 |
| 4,478,083 | A | 10/1984 | Hassler |
| 4,485,819 | A | 12/1984 | Igl ............................ 128/660 |
| 4,567,896 | A | 2/1986  | Barnea et al. .............. 128/660 |

(Continued)

FOREIGN PATENT DOCUMENTS

WO    WO 83/02053    6/1983

OTHER PUBLICATIONS

Jan Bolmgren, Bertil Jacobson and Bjorn Nordenstrom, "Stereotaxic Instrument for Needle Biopsy of the Mamma" J Roenigenal 129:121-125, Jul. 1977.

*Primary Examiner*—Ruth S Smith
(74) *Attorney, Agent, or Firm*—Lindsay Mcguiness

(57) ABSTRACT

The present invention provides for x-ray imaging and ultrasound imaging of a body region of interest in a spatially correlatable manner. The resultant x-ray and ultrasound images may be combinatively employed to provide three-dimensional information regarding a location of interest within the body, and is particularly apt for use in the analysis/biopsy of potential lesions and suspicious masses in a female breast. The invention provides for direct body contact by an ultrasound imaging head, as well as targeted ultrasound imaging of a selected portion of the region from which x-ray images are obtained. A user interface system facilitates various procedures including ultrasound guided needle biopsy procedures.

19 Claims, 20 Drawing Sheets

U.S. PATENT DOCUMENTS

| | | | |
|---|---|---|---|
| 4,576,175 A | 3/1986 | Epstein | 128/660 |
| 4,613,122 A | 9/1986 | Manabe | 269/322 |
| 4,618,973 A | 10/1986 | Lasky | 378/37 |
| 4,625,555 A | 12/1986 | Fujii | 73/597 |
| 4,671,292 A | 6/1987 | Matzuk | 128/660 |
| 4,727,565 A | 2/1988 | Ericson | 378/205 |
| 4,750,487 A | 6/1988 | Zanetti | 128/303 |
| 4,791,934 A | 12/1988 | Brunnett | 128/653 |
| 4,869,247 A | 9/1989 | Howard, III et al. | 128/303.1 |
| 4,875,478 A | 10/1989 | Chen | 128/303 |
| 4,890,311 A | 12/1989 | Saffer | 378/99 |
| 4,899,756 A | 2/1990 | Sonek | 128/662.05 |
| 4,930,143 A | 5/1990 | Lundgren et al. | 378/37 |
| 5,078,142 A | 1/1992 | Siczek et al. | 128/653.1 |
| 5,129,911 A | 7/1992 | Siczek et al. | 606/130 |
| 5,285,772 A | 2/1994 | Rattner | 128/24 |
| 5,289,520 A | 2/1994 | Pellegrino et al. | 378/37 |
| 5,320,111 A | 6/1994 | Livingston | 128/754 |
| 5,398,690 A | 3/1995 | Batten et al. | 128/662.05 |
| 5,409,497 A | 4/1995 | Siczek et al. | 606/130 |
| 5,411,026 A | 5/1995 | Carol | 128/660.03 |
| 5,415,169 A | 5/1995 | Siczek et al. | 128/653.1 |
| 5,447,154 A | 9/1995 | Cinquin et al. | 128/653.1 |
| 5,474,072 A | 12/1995 | Shmulewitz | 128/660.09 |
| 5,479,927 A | 1/1996 | Shmulewitz | 128/660.09 |
| 5,499,630 A | 3/1996 | Hiki et al. | 128/662.05 |
| 5,512,137 A * | 4/1996 | Shimizu et al. | 162/198 |
| 5,526,394 A | 6/1996 | Siczek et al. | 378/37 |
| 5,569,266 A | 10/1996 | Siczek | 606/130 |
| 5,584,292 A | 12/1996 | Cheung | 128/653.1 |
| 5,609,152 A | 3/1997 | Pellegrino et al. | 128/653.1 |
| 5,647,373 A | 7/1997 | Paltieli | 128/749 |
| 5,660,185 A | 8/1997 | Shmulewitz et al. | 128/749 |
| 5,664,573 A | 9/1997 | Shmulewitz | 128/660.09 |
| 5,776,062 A * | 7/1998 | Nields | 600/407 |
| 5,833,627 A | 11/1998 | Shmulewitz et al. | 600/562 |
| 5,983,123 A * | 11/1999 | Shmulewitz | 600/407 |
| 6,019,725 A | 2/2000 | Vesely et al. | 600/447 |
| 6,102,866 A * | 8/2000 | Nields et al. | 600/461 |
| 6,459,925 B1 * | 10/2002 | Nields et al. | 600/427 |
| 6,574,499 B1 * | 6/2003 | Dines et al. | 600/427 |

* cited by examiner

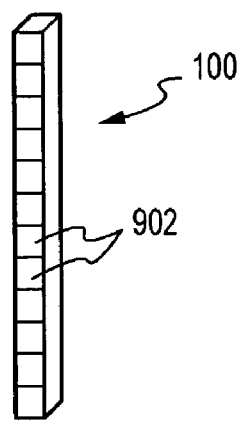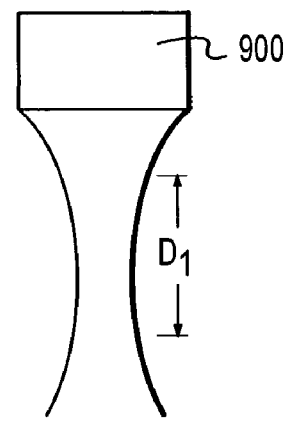
FIG.9A  FIG.9B
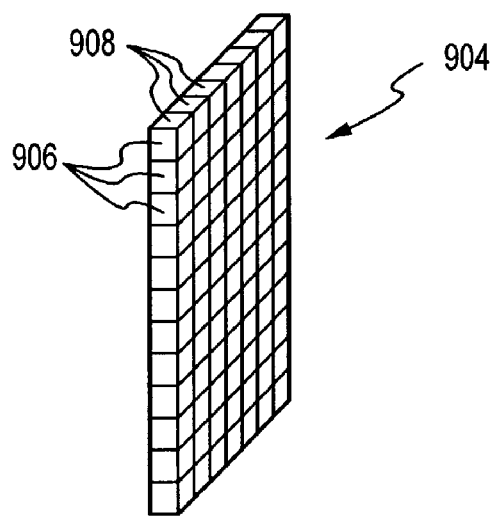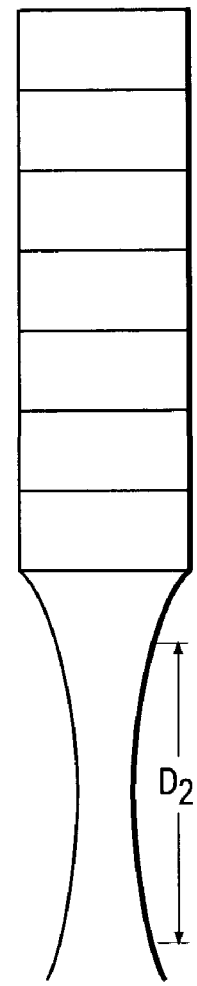
FIG.9C  FIG.9D

SALLY JOBE BREAST CENTRE
MAMMOTEST PROCEDURE

PATIENT NAME: ULTRA _____ (FIRST NAME)
               (LAST NAME)

PATIENT I.D.#: _____ DATE OF PROCEDURE: 04-26-98

PHYSICIAN: _____ TECH'S INITIALS: _____

REMARKS:

DONE
CANCEL

? HELP
LATERAL APPROACH
TARGET ON SCOUT
PRINT DB ENTRY

PLEASE USE KEYBOARD TO ENTER PATIENT DATA.

CLICK "DONE" WHEN YOU ARE FINISHED (PATIENT NAME MUST BE ENTERED TO PROCEED)

FIG.11

SPATIALLY CORRELATED X-RAY AND ULTRASOUND MAMMOGRAPHIC IMAGING SYSTEMS AND METHOD

RELATED APPLICATION INFORMATION

This application is a divisional of U.S. patent application Ser. No. 09/449,267, filed Nov. 24, 1999, now U.S. Pat. No. 6,459,925, issued Oct. 1, 2002, which claims the benefit of U.S. Provisional Application Ser. No. 60/109,881, filed on Nov. 25, 1998 and is a Continuation-in-Part of Ser. No. 09/111,094, filed on Jul. 6, 1998, now U.S. Pat. No. 6,102,866, issued Aug. 15, 2000, all of which are incorporated herein by reference in their entireties. The latter application is a continuation-in-part of U.S. patent application Ser. No. 08/730,107, filed Oct. 15, 1996 now issued as U.S. Pat. No. 5,776,062.

FIELD OF THE INVENTION

The present invention relates to medical imaging/biopsy systems, and more particularly, to an enhanced system that employs x-ray imaging and targeted ultrasound imaging in a combinative, spatially correlatable manner that is particularly apt for breast imaging/biopsy procedures. The invention further relates to targeted ultrasound features that yield plural modalities of operation as well as improved biopsy capabilities and a user interface system for facilitating targeting of a medical instrument to an area of interest within a patient's breast.

BACKGROUND OF THE INVENTION

The benefits of early detection and tissue diagnosis of potential lesions and/or suspicious masses within the body is now well established. Indeed, as medical practice and managed care plans continue to evolve, the role of early detection and tissue diagnosis is ever-increasing. With such emphasis, both efficacy and efficiency are at a premium. Specifically, reduction of the time requirements of highly trained medical personnel, patient office visits and medical equipment costs (e.g., via use of multiple-purpose equipment) are primary objectives for procedures utilized in the early detection and tissue diagnosis of potential lesions and otherwise suspicious masses.

Of particular ongoing interest is the area of mammography and breast biopsy. Currently, it is common for patients to receive regular screening mammograms, wherein two x-ray images are generated for each breast in order to identify potential lesions or masses suspicious for malignancy. In the event of equivocal screening mammograms, further x-ray or ultrasound imaging/exams may be performed to obtain additional information. The obtainment of a diagnostic mammogram and/or an ultrasound exam requires another patient office visit and additional medical personnel time. For example, if the presence of a suspicious mass is confirmed, an ultrasound procedure may be performed in order to further characterize the mass. Specifically, a free-hand procedure can be performed in which a hand-held ultrasound probe is manipulated on the breast while viewing a display to obtain depth-profile information. As can be appreciated, location of a potential lesion/suspicious mass can be difficult, and the ultrasound images obtained are frequently difficult to mentally associate with the x-ray images. As such, the ability to utilize ultrasound technologists as opposed to experienced physician specialists to perform most breast ultrasound procedures is limited.

Should a breast lesion show signs of malignancy pursuant to diagnostic mammography or ultrasound, a breast biopsy is typically performed. Needle localized surgical biopsy means have recently been giving way to stereotactic x-ray biopsy with automated core needles and tissue removal systems. A patient is typically positioned prone (e.g., on a solid table) with the breast immobilized within a predetermined frame of reference (e.g., the breast passes through an opening in the table and is immobilized between opposing compression plates). Stereotactic X-ray images are then generated (e.g., via x-ray film or digital imaging) for review by medical personnel to identify a specific location of interest (e.g., corresponding with a potential lesion or suspicious mass) within the predetermined frame of reference. A puncture instrument, mounted in predetermined relation to the predetermined frame of reference, is then positioned/utilized to obtain a sample of tissue from the location of interest. Of note, current state-of-the-art breast biopsy systems include the MAMMOTEST®, MAMMOVISION® and SENOSCAN™ products offered by Fischer Imaging Corporation of Denver, Colo. Such systems are further described in U.S. Pat. Nos. 5,078,142, 5,240,011, 5,415,169, 5,526,394 and 5,735,264, hereby incorporated by reference in their entirety.

While breast lesions may typically be biopsied utilizing stereotactic x-ray imaging, only recently have technical improvements in ultrasound allowed certain lesions to be biopsied under ultrasound guidance (i.e., with hand-held ultrasound probe and/or biopsy means). In this regard, ultrasound may be preferred due to the lack of ionizing radiation and the established availability of real time imaging to reduce procedure time.

Recent developments in tissue removal systems have resulted in larger, heavier devices that are difficult for a physician to use in conjunction with free-hand ultrasound guidance. As an example, the MAMMOTOME™ from Biopsys Medical, Inc. of Irvine, Calif. allows rapid removal of breast tissue through a small puncture hole in the breast. Due to the weight and size of the device, physicians are performing more stereotactic x-ray procedures with the MAMMOTOME™ due to the solid support of the device by prone stereotactic tables.

In the event that analysis of tissue by histopathologic techniques indicates that a lesion or undesirable mass should be removed from a breast, the surgeon will typically review the various breast images previously obtained to develop a therapeutic surgical strategy, with the goal of removing the entire potential lesion and/or suspicious mass while achieving acceptable cosmetic results.

SUMMARY OF THE INVENTION

It is an object of the present invention to provide an enhanced imaging/biopsy system that can reduce trained medical personnel time requirements in diagnostic and biopsy procedures for tissue diagnosis. It is a related objective to provide such a system in a cost-effective manner; namely through the provision of a system having relatively expensive components that can be utilized for multiple medical procedures combinatively employed in a single system.

A further objective of the present invention is to provide an enhanced imaging/biopsy system for obtaining spatially correlated three-dimensional image information regarding a location of interest in the body, such system being apt for the obtainment of three-dimensional image information regarding a potential lesion or suspicious mass in a female patient's breast. It is a further objective to provide such information in a manner allowing for enhanced use of tissue removal systems used for obtaining tissue samples from the body, including specifically, tissue from a potential lesion or suspicious mass within a female patients breast. Such information may also be used in conjunction with other targeted instruments such as guide wire placement devices and instruments for ablation, delivery, etc.

Yet another objective of the present invention is to provide an enhanced imaging/biopsy system for obtaining depth-related image information for diagnostic use and for otherwise yielding biopsy-related control and access advantages.

These objectives and additional advantages are met by various aspects of the present invention. In this regard, one aspect of the present invention provides for the combinative use of x-ray imaging and targeted ultrasound imaging. More particularly, this inventive aspect provides for the transmission of x-ray radiation through a selected body region-of-interest within a predetermined, three-dimensional frame of reference to obtain x-ray image data corresponding with one or more x-ray images. Additionally, an ultrasound signal is directed into a limited, selectively targeted portion of the x-rayed body region of interest to provide ultrasound image data corresponding with one or more ultrasound images of the targeted portion of the selected body region. The x-ray and ultrasound image data are acquired in spatial co-relation by utilizing x-ray imaging means and ultrasound imaging means each supportably positioned in known co-relation to the predetermined, three-dimensional frame of reference. This arrangement allows the x-ray and ultrasound image data to combinatively provide correlated, three-dimensional image data corresponding with the body region of interest. In turn, the spatially correlated information allows for an enhanced medical diagnosis of a given location of interest within the body region (e.g., potential lesion or suspicious mass in a breast application) and enhanced biopsy options in relation thereto.

In an additional aspect of the present invention, an ultrasound imaging means is provided that is advantageously positionable in direct contact with the body region of interest for optimal ultrasound image acquisition. More particularly, in breast imaging applications, opposing compression plates may be employed to immobilize a patient's breast within the predetermined, three-dimensional frame of reference, wherein an opening is provided in one of the compression plates for selectively positioning an ultrasound imaging head (e.g., comprising a linear ultrasound transducer array) therethrough in contact with the patient's breast for imaging. The ultrasound imaging means may be positioned below and on either side of a center axis of a patient support table, or alternatively, may be positioned below and in substantially coaxial relation to a patient support table.

In another aspect of the present invention, a locating means (e.g., an image data processor with display/user interface) is provided for using x-ray and ultrasound image data to identify a particular location of interest within the body region of interest; and a biopsy means is provided for obtaining a sample from the identified location of interest. In this regard, the biopsy means may include positioning means for selectively and supportably positioning an elongated puncture instrument or other tissue removal system relative to the predetermined, three-dimensional frame of reference, including for example positioning at a desired entry angle.

In a further aspect of the present invention, an ultrasound imaging means is provided that comprises a means for selectively positioning an elongated ultrasound imaging head in a known position relative to the predetermined, three-dimensional frame of reference, including angulation of the ultrasound imaging head relative to the predetermined frame of reference. In the latter regard, the imaging head may be angled to image a layer, or "slice," of the body region of interest from a direction orthogonal to a direction from which an angled puncture instrument or other tissue-removal system may be advanced within such layer (i.e., the longitudinal axes of the imaging head and puncture instrument are substantially parallel). Such ultrasound imaging allows for processor simulation/display of a biopsy procedure using a tissue-removal system from a given biopsy position, as well as real-time imaging/control of a biopsy device as it is actually advanced into the body region of interest.

In an additional aspect of the present invention, an ultrasound imaging means is provided that comprises a positioning means for supportably and selectively positioning an ultrasound imaging probe in known spatial relation to the predetermined, three-dimensional frame of reference, while also and alternatively allowing the ultrasound imaging probe to be disengaged from the positioning means and manually manipulated in hand-held procedures. More particularly, the positioning means may comprise a holder means for selectively receiving an ultrasound imaging probe that is also adapted for hand-held use, wherein the probe may be selectively employed for hand-held manipulation or alternatively positioned within the holder means (e.g., via sliding and/or "snap-in" engagement). In the later regard, the positioning means may be employed to supportably position the ultrasound imaging probe in predetermined relation relative to the predetermined three-dimensional frame of reference to obtain depth information in a desired layer, or "slice" of the body region of interest. Further, the positioning means may comprise one or more drive means for providing at least partial automated positioning of the ultrasound imaging probe (e.g., for automated X and/or Y dimension positioning and/or for automated rotational positioning about a Z axis within an XY plane).

As indicated above, x-ray images may be employed to select a limited, or targeted, portion of the x-rayed body region of interest to be imaged utilizing the ultrasound signal. Such targeted ultrasound imaging avoids the acquisition, storage and processing of unneeded imaging data, and otherwise facilitates efficient use of medical personnel time, and otherwise advantageously accommodates direct contact with the body portion to be imaged. Further, where necessary, the provision of a hand-held ultrasound imaging option provides practitioners with added flexibility as may be desirable in certain applications.

According to a further aspect of the present invention, an ultrasound imaging apparatus is provided that has an improved imaging focal depth. It has been noted that a linear array of transducer elements may have a focal depth that is only a portion of the thickness of a patient's immobilized breast. In this regard, in order to provide for more complete imaging for a range of patients, it is desirable to provide a greater focal depth. In particular, it would be desirable to provide a focal depth approaching to accommodate a range of patients and procedures. A corresponding apparatus with improved focal depth includes a probe structure supporting a transducer array that includes at least a first set of transducer elements disposed a first distance from the signal interface surface of the probe structure and a second set of transducer elements disposed a second distance from the signal interface surface. The first and second sets of elements thereby provide a combined focal depth that is greater than the focal depth that would be provided by either of the transducer sets considered alone. In a preferred implementation, a transducer array includes 7 or more columns of array elements where each column is disposed a different distance from the signal interface surface of the probe structure. Such a structure provides for improved imaging for a range of patients.

In accordance with a still further aspect of the present invention, a display is provided proximate to the patient's breast in order to facilitate real time monitoring of insertion of a medical instrument into the patient's breast. The associated apparatus includes: an immobilizer for immobilizing the patient's breast; a first graphical display for displaying one or more images of the patient's breast so as to permit identification of an area of interest within the patient's immobilized breast; a medical instrument operative for insertion to the identified area of interest within the patient's breast; and a second graphical display, separate from the first graphical display and located proximate to the patient's immobilized breast, for providing real time images of the patient's compressed breast so that a user can monitor insertion of the medical instrument to the identified location of interest using the second graphical display located proximate to the patient's immobilized breast. Preferably, the second graphical display can be translated and rotated to facilitate viewing during a medical procedure In one embodiment, the patient is supported in a prone position on a table with the breast under examination protruding through an opening in the table and the second display is disposed beneath the table for convenient viewing. Real time images such as ultrasound images can be monitored on the second display during insertion of a medical instrument such as a biopsy needle for improved guidance and confidence regarding sampling of suspicious masses.

According with a still further aspect of the present invention, an improved graphical interface is provided for guiding a user through a medical procedure. The associated method includes the steps of: providing a mammographic medical device for use in performing a medical procedure on a patient's breast; providing a display device having a graphical viewing area; providing a processor operative to drive the display device so as to display selected information in the viewing area; operating the display device using the processor to provide a first display whereby the user is presented with options corresponding to different operating modes of the medical device; operating the processor in response to an input regarding the operating mode to provide instructions for operating the medical device to obtain first and second images, where at least one of the images is an ultrasound image; operating the processor to display the images in a first portion of the graphical viewing area and provide graphical objects in a second portion of the viewing area for use in entering information related to the medical procedure; and using the first and second images to perform a medical procedure on the patient's breast.

Preferably, one of the images is an x-ray image and the other image is an ultrasound image. In response to prompts provided via the display device, the user can identify a location of interest within the patient's breast on each of the first and second images. The user may also enter certain image enhancement functions and enter additional information such as needle type using the display device. In one implementation, the processor is operative for displaying a projected penetration path of a medical instrument in superimposition on at least one of the images. The processor may further be operative for comparing an actual penetration path to the projected penetration path to identify any deviation therebetween and, if desired, to provide appropriate warnings. The graphical user interface system thereby provides enhanced functionality, provides simple to follow instructions for medical personnel and allows for close monitoring of a medical procedure for increased accuracy and confidence in the results.

Additional features and advantages of the present invention will become apparent upon consideration of the further description provided herein.

DESCRIPTION OF THE DRAWINGS

FIG. 9A is a schematic diagram of a linear ultrasound probe head array in accordance with the present invention.

FIG. 9B is a schematic diagram illustrating an ultrasound signal profile for the probe of FIG. 9A.

FIG. 9C is a schematic diagram of a planar ultrasound probe head array in accordance with the present invention.

FIG. 9D is a schematic diagram showing an ultrasound signal profile for the probe head of FIG. 9C.

FIGS. 10-20 show various screens of a user interface system in accordance with the present invention.

DETAILED DESCRIPTION

Figure 1:
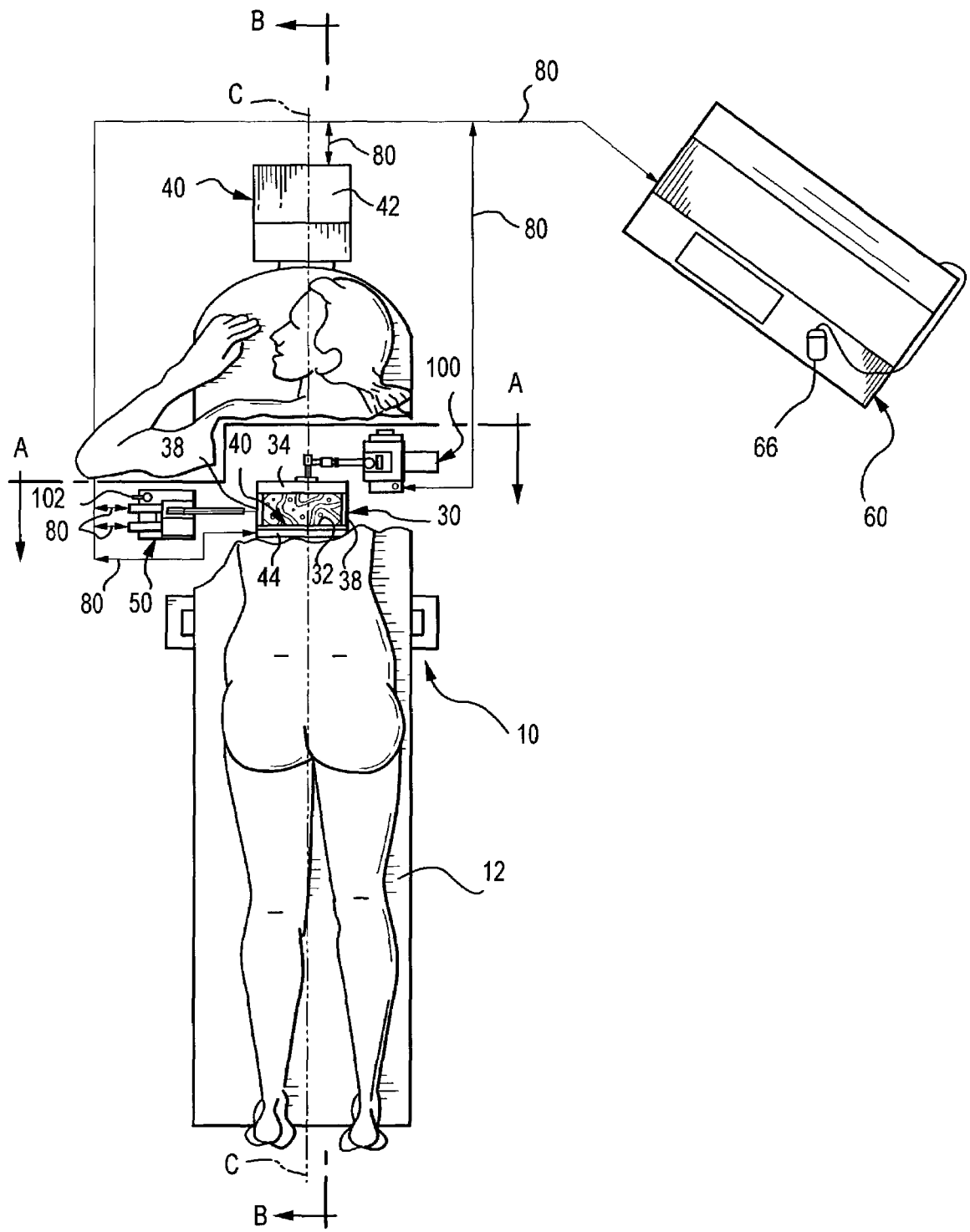
FIG. 1 is a top view of a stereotactic x-ray imaging system with integrated ultrasound imaging and biopsy components combinatively defining one embodiment of the present invention with a central patient/table portion cutaway to show key components.

FIGS. 1-6 illustrate one embodiment of a diagnostic ultrasound/x-ray biopsy system comprising the present invention, as adapted for mammography/breast biopsy use.

Generally, the system comprises a support assembly 10 having a patient table 12 with breast-opening 14 therethrough, an immobilization assembly 30 for immobilizing a patient's breast within a predetermined XYZ frame of reference under the opening 14 of table 12, an x-ray imaging assembly 40 for providing two-dimensional x-ray images (e.g., X-Y images) of the patient's immobilized breast in correlated spatial relation to the predetermined XYZ frame of reference, and an ultrasound imaging assembly 100 for providing orthogonal depth-profile images (e.g., X-Z, Y-Z and/or X,Y-Z images) of the immobilized breast in correlated spatial relation to the predetermined XYZ frame of reference. A biopsy assembly 50 having puncture instrument 52 is also provided for obtaining samples from a patient's breast while the breast is immobilized in the predetermined XYZ frame of reference. A display/processor assembly 60 is provided for recording/displaying the various images obtained/generated, for determining the coordinates of a user-identified location of interest within the breast and for monitoring/controlling/simulating the position of the various positionable assembly components.

As will be appreciated, the illustrated embodiment may utilize the x-ray, automated biopsy and other functionalities embodied in the current MAMMOTEST® and MAMMOVISION® products of Fischer Imaging Corp. of Denver, Colo., U.S.A. In this regard, the present invention allows for the integration and effective use of ultrasound imaging with such products, thereby allowing medical equipment cost efficiencies to be realized. As noted previously, the MAMMOTEST® and MAMMOVISION® products include features corresponding with the disclosures in U.S. Pat. Nos. 5,078,142, 5,240,011 and 5,415,169, and 5,735,264, which are incorporated by reference in their entirety.

Support assembly 10 further includes pedestal 16 and cantilevered first and second support arms 20 and 22, respectively, for supportably interfacing the breast immobilization assembly 30, x-ray imaging assembly 40, ultrasound imaging assembly 100 and biopsy assembly 50 in a predetermined spatially correlated manner. First and second supports arms 20 and 22 can be jointly pivoted relative to pedestal 16, thereby providing imaging/biopsy access to the breast from different directions (e.g., 0°, +90° and −90° relative to the table longitudinal axis). Additionally, second support arm 22 can be selectively pivoted relative to first support arm 20, to provide for stereotactic x-ray imaging (e.g., +15° and −15° relative to the first support arm longitudinal axis).

Breast immobilization assembly 30 is supported on first support arm 20 and includes a stationary face plate 32 and opposing compression paddle 34 for immobilizing a patient's breast therebetween. Compression paddle 34 is x-ray transmittent and further includes a window 36 for direct breast access by the ultrasound imaging assembly 100 and/or biopsy assembly 50. Compression paddle 34 is selectively positionable along first support arm 20 (e.g., via motorized and position sensor systems) for controlled, registered movement toward/away from face plate 32 to accommodate breast positioning/removal and differing breast sizes. Compression paddle 34 can be readily removed from/interconnected to the first support arm 20 to accommodate the selective use of compression paddles of differing sizes, shapes, window positions, etc. As shown in FIG. 1, compression assembly 30 may further include selectively advanceable/retractable auxiliary side paddles 38, each having optional openings for breast access (e.g., by a puncture instrument or an ultrasound imaging head) for further compression/breast immobilization within the predetermined XYZ frame of reference, and particularly during use of biopsy assembly 50. In this regard, compression paddle 34 and face plate 32 are intended to define a breast imaging area of substantially common thickness and to immobilize such area during imaging/biopsy procedures, and to otherwise provide direct access to the breast for targeted ultrasound imaging/biopsy procedures.

X-ray imaging assembly 40 includes x-ray tube source 42 mounted on the end of second support arm 22 and x-ray receiver/imager 44 mounted on first support arm 20. As will be appreciated, x-ray tube source 42 provides x-ray radiation having a center axis C substantially perpendicular to the fronts of face plate 34 and x-ray receiver/imager 44, such x-ray radiation having a focal point positioned along the center axis C at a determinable location between the face plate 32 and compression paddle 34 during use. In this regard, and by way of example only, the predetermined XYZ frame of reference can be defined in the illustrated embodiment in relation to an X-Y plane corresponding with the front surface of the face plate 32 and/or parallel back surface of compression paddle 34, together with orthogonal X-Z and Y-Z planes within which the x-ray radiation center axis passes (i.e., all three planes being orthogonal). X-ray opaque markings (not shown) can be provided on compression paddle 34 and/or face plate 32 to facilitate spatial correlation of the radiation center axes and x-ray receiver/imager.

In the illustrated embodiment, the x-ray receiver/imager 44 is disposed in abutting relation with the face plate 32. X-ray receiver/imager 44 may comprise an image receptor consisting of a removable radiographic film cassette (e.g., for full-field breast imaging) and/or digital camera (e.g., for partial field, real-time imaging/display). In the latter regard, a partial field, digital CCD camera 46 (e.g., having a 5 mm×10 mm or 5 mm×5 mm imaging area) may be disposed for selective, driven XY movement (e.g., via a servo-drive arrangement) in registered relation to the predetermined XYZ frame of reference.

In the illustrated embodiment, ultrasound imaging assembly 100 and biopsy assembly 50 are selectively and alternatively connectable to opposing sides of first support arm 20 via connection/locking handles 102 and 55, respectively. Additionally, biopsy assembly 50 may be mounted in an axially aligned manner on first support arm 20 for breast access through window 36. A reference, or "home," position for each assembly in a given mounted location is known relative to the predetermine XYZ frame of reference. Further, positioning of the various components of each assembly during use is automatically determinable via position sensor/control systems. As will be appreciated, such positioning can be automated via corresponding processor-controlled, servo motors.

Biopsy assembly 50 comprises a punction sub-assembly 54, which includes puncture instrument 52, and positioner sub-assembly 56. Positioner sub-assembly 56 includes horizontal axis and vertical control motors 58 and 60, respectively, for selective sideward movement and upward angulation of the punction instrument 52. By way of example, punction sub-assembly 56 may comprise the AUTOGUIDE™ assembly of Fischer Imaging Corporation. As will become appreciated, the illustrated embodiment may be particularly apt for use with punction subassemblies for obtaining samples having relatively large cross-sections, including, for example, the MAMMOTOME™ from Biopsys Medical, Inc. of Irvine, Calif.

Ultrasound imaging assembly 100 comprises an ultrasound imaging head, or probe, 110 interconnected to arm assembly 130 and, in turn, to XYZ ultrasound positioning assembly 140. As will be further explained, XYZ ultrasound positioning assembly 140 is employed to selectively position ultrasound imaging head 110 through the window 36 of compression paddle 34 to establish direct breast contact for targeted ultrasound imaging in determinable spatial relation to the predetermined XYZ frame of reference.

Figure 5:
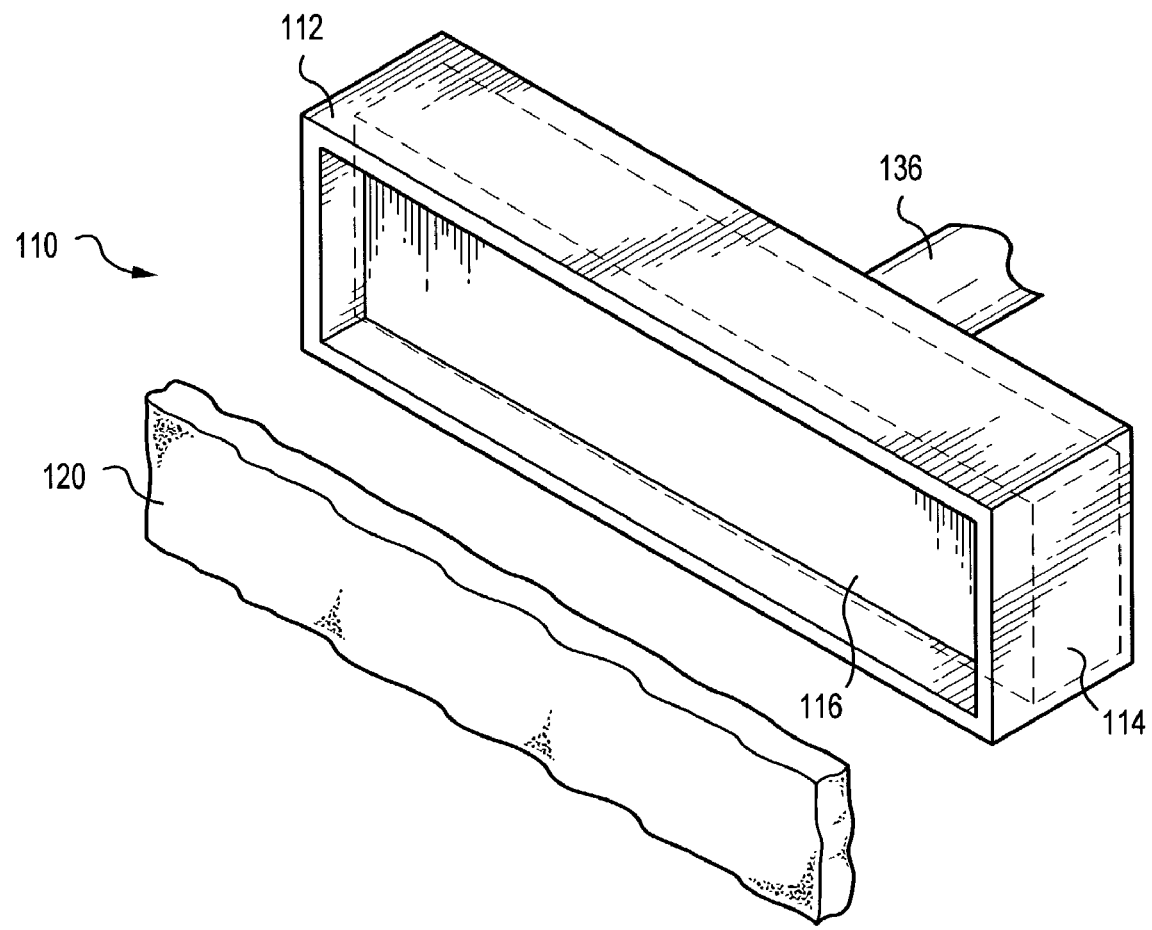
FIG. 5 is a perspective view of an ultrasound imaging head employable in the present invention.

As shown in FIG. 5, ultrasound probe 110 may include an elongated housing 112 with an elongated ultrasound transducer module 114 positioned therein. Ultrasound transducer module 114 provides an ultrasound signal having a focal point on a signal center axis at a location between compression paddle 34 and face plate 32. Ultrasound transducer module 114 may include, for example, a phased linear array of ultrasound transducers positioned along a longitudinal axis of the ultrasound probe 110. The ultrasound probe 110 emits signal pulses and detects corresponding echo pulses to generate the depth-profile images. More particularly, and as will be appreciated by those skilled in the art, detected echo pulses will result from ultrasound transmissivity differences (i.e., ultrasound impedance mismatches) at tissue-type transition areas (e.g., transitions between healthy tissue and a potential lesion/suspicious mass) and at structural obstructions (e.g., the front surface of face plate 32). The housing 112 of ultrasound probe 110 may include a recess 118 (exaggerated in FIG. 5) for receiving a cold-pack 120 for orthogonal application to a biopsy site after a biopsy procedure. Applying pressure and a cold medium directly over a biopsy site in the breast has been shown to reduce hematoma bleeding and bruising.

XYZ ultrasound positioning assembly 140 includes X, Y and Z platforms 142, 146 and 148, respectively, mounted for selective, registered movement on corresponding support members 152, 156 and 158 relative to the predetermined XYZ frame of reference. In this regard, XYZ positioning assembly 140 may include internal X, Y and Z optical position encoders. XYZ positioning assembly 140 can further include X, Y and Z motor drives for automatic, selective positioning of ultrasound imaging head 110 in registered XYZ relation to the predetermined XYZ frame of reference. The XYZ positioning assembly 140 may also include counterbalance and electro-lock components to accommodate ready manual positioning and to maintain a selected ultrasound imaging/biopsy position, respectively.

Arm assembly 130 is provided to allow the ultrasound imaging probe 110 to be rotated about one or more of selected X, Y and Z axes to obtain a desired pitch, roll and/or yaw orientation). For example, arm assembly 130 can be controlled to selectively rotate the longitudinal axis, or pitch, of probe 110 so that the ultrasound signal may be employed to obtain depth-profile image in a plane, or "slice," within which an upwardly angled punction instrument 52 of biopsy assembly 50 may be orthogonally advanced, as will be further discussed.

In the illustrated embodiment, arm assembly 130 includes pivot arm 132 pivotally interconnected to XYZ ultrasound positioning assembly 140 via a lock/release mechanism (not shown) for selective, centered rotation of probe 116 about axis YY.

Arm assembly 130 further includes arm 134 rotatably interconnected to arm 132 via a lock/release mechanism (not shown) for selective, centered rotation of probe 116 about axis XX, and arm 136 rotatably interconnected to arm 134 via a lock/release mechanism (not shown) for selective, centered rotation of probe 116 about axis ZZ. Internal optical encoders (not shown) may be provided at the various arm interconnections, wherein the pitch, roll and/or yaw of probe 110 is automatically determinable in relation to the predetermined XYZ frame of reference. In this regard, internal automated micro-positioners may also be utilized under processor control.

As will be appreciated, the ultrasound signal may be scanned to obtain depth-profile information for a predetermined layer, or "slice," within the region of interest. By way of primary example, such scanning may be provided electrically by driving a phased linear array of transducers comprising probe 110 in a known manner and/or via manual or automatic-driven control of XYZ positioning assembly 140 to mechanically move ultrasound imaging head 110.

Figure 6:
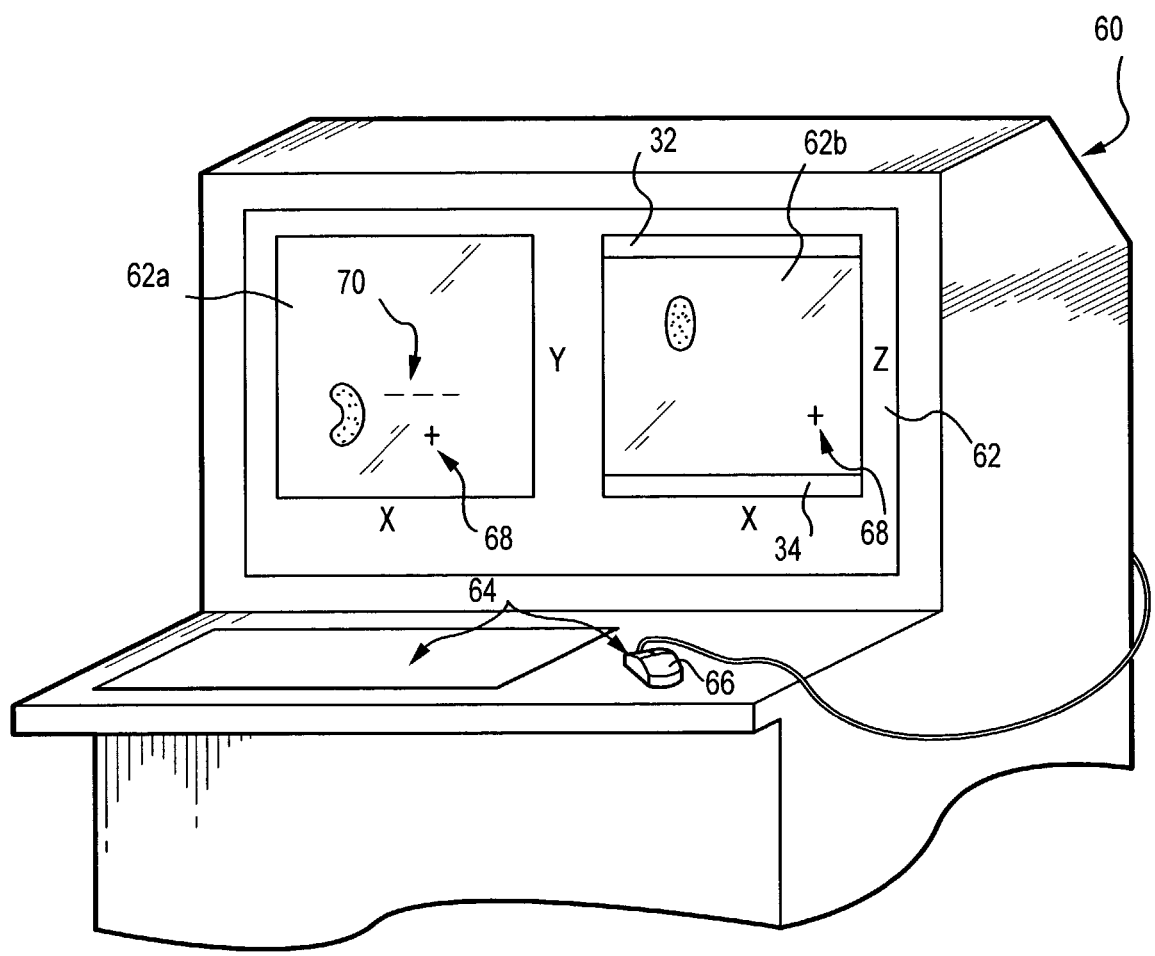
FIG. 6 illustrates spatially correlated x-ray and ultrasound images of a potential breast lesion/suspicious mass obtainable with the present invention.

As shown in FIG. 6, display/processor 60 includes a display screen 62 for displaying the acquired x-ray images on a first portion 62a and displaying corresponding depth-profile ultrasound images on a second portion 62b, each in registered co-relation to the predetermined XYZ frame of reference. Display/processor 60 may further include a user interface means 64, e.g., keyboard 65 and mouse 66 and screen point cursor 68 (e.g., on both display portions 62a, 62b), wherein a user may identify (e.g., click upon) a specific location-of-interest within both an x-ray image and corresponding ultrasound image (e.g., corresponding with a potential lesion or suspicious mass), e.g., for automatic processor determination of the three-dimensional coordinates of the location within the predetermined XYZ frame of reference. User interface means may further allow for user selection/display of a particular desired ultrasound depth-profile image, e.g., via mouse 66 and screen "slice" cursor 70 on the x-ray image display portion 62a. More particularly, screen "slice" cursor 70 may be employed to identify a particular slice, or layer, of an X-Y x-ray image for which a corresponding ultrasound depth-profile image is to be obtained (e.g., thereby resulting in processor-assisted positioning and imaging using probe 110) and/or accessed and displayed (e.g., where such ultrasound depth-profile image has been previously obtained/stored for selective subsequent review).

As indicated, display/processor 60 may be operatively interconnected (e.g., via electrical lines 80) to the various positionable assembly components for monitoring/controlling their respective positions relative to the predetermined XYZ frame of reference, including the positionable components of immobilization assembly 30, x-ray imaging assembly 40, ultrasound imaging assembly 110 and biopsy assembly 50. By way of primary example, display/processor 60 may determine the three-dimensional coordinates of a specific location of interest, as described above, and in turn assist/control the positioning of biopsy assembly 50 so as to position the assembly for obtainment of a tissue sample from the location of interest. In this regard, the display/processor 60 may also be employable to visually project, or simulate, the entry of a punction instrument 52 into a given location of interest, thereby allowing physicians the opportunity to insure an optimal positioning for biopsy entry prior to an actual biopsy procedure. Since three-dimensional visualization of a potential lesion/suspicious mass can be provided by the present invention, and since the disclosed arrangement allows for breast access by biopsy assembly 50 from a plurality of aspects (e.g., by selective mounting on either side of or coaxial along support arm 20), such simulated biopsy modeling may prove to be of particular advantage.

The present invention allows for spatial correlation of the x-ray and ultrasound images utilizing various techniques. By way of primary example, it can be appreciated that the X-Y x-ray images obtained can be readily correlated to the predetermined XYZ frame of reference since the position and attributes of x-ray source 42 and x-ray receiver/imager 44 are each known in relation to the predetermined XYZ frame of reference. Additionally, in stereotactic imaging procedures, the two X-Y stereotactic x-ray images can be employed to obtain a Z location for particular location of interest relative to the predetermined XYZ frame of reference utilizing known triangulation techniques, as will be appreciated by those skilled in the art. Further, the XYZ positioning of ultrasound imaging head 110 is determinable relative to the predetermined XYZ frame of reference, as noted above. Relatedly, in the embodiment described above, the ultrasound imaging head 110 will emit/detect ultrasound signals in substantially the same plane as the surface of compression paddle 34 contacting the imaged breast. The position of such surface relative to the predetermined XYZ frame of reference (e.g., the Z distance to face plate 32) is also determinable. In view of the foregoing, it can be seen that utilizing known ultrasound pulse/echo techniques a depth profile comprising a potential lesion/suspicious mass can be spatially related in a reliable manner to the acquired x-ray images.

In use, a patient can be positioned on the table 12 with a breast positioned through opening 14. Compression paddle 34 is then advanced along first support arm 20 to compress the breast to define a cross-sectional imaging area having a common thickness and to otherwise immobilize the breast in a set position within the predetermined XYZ frame of reference. X-ray imaging assembly 40 is then selectively positioned to obtain the desired x-ray images. Such x-ray images are then reviewed using display/processor 60, to identify, analyze and or otherwise confirm the presence and location of a potential lesion or suspicious mass for ultrasound imaging. Alternatively, the general location of a potential lesion or suspicious mass may already be known due to prior x-ray screening.

In either case, to proceed with ultrasound imaging, the patient should be positioned/repositioned so that the potential lesion or suspicious mass is positioned within the accessible field of view of ultrasound imaging head 110 when it is maneuvered through the window 36 of compression paddle 34 in direct contact with the imaged breast. As can be appreciated, in order for the present invention to yield spatially correlatable image information with respect to a potential lesion or suspicious mass, new x-ray and corresponding ultrasound images should be generated for each position in which a breast is immobilized within the predetermined XYZ frame of reference. As such, the benefit of utilizing a digital camera 46 in x-ray receiver 44 for partial field, real-time imaging via display/processor 60 can be readily understood.

Once it is verified that the area of interest is positioned adjacent to the window 36, ultrasound imaging probe 110 is positioned through the window 36 and a series of ultrasound images are obtained and displayed on display/processor 60. Cursor 66 control of the ultrasound images taken across the area of interest provides additional, valuable information as to the type of potential lesion/suspicious mass originally noted on an original mammogram. For example, with proper training of ultrasound and x-ray imaging techniques, physicians may rule out the possibility of a solid mass in favor of a fluid-filled cyst. Or, additional ultrasound characteristics may aid the physician in making a definitive diagnosis.

If it is determined that a biopsy is desired, the specific location from which tissue is to be obtained can be identified using mouse 66 to position screen point cursor 68 on both the x-ray image and correlated ultrasound depth-profile image on display/processor 60. Three-dimensional coordinates can then be determined and utilized by display/processor 60 to control positioning of biopsy assembly 50. In this regard, it will be appreciated that specific attributes of the particular punction subassembly 54 utilized will have been previously entered into by display/processor 60. Further, and as noted above, given such previous input information, display/processor 60 may be employed to simulate the advancement of punction instrument 52 into the breast from a given potential position, thereby allowing the physician to determine if breast biopsy access from a different position may be more desirable.

Figure 2:
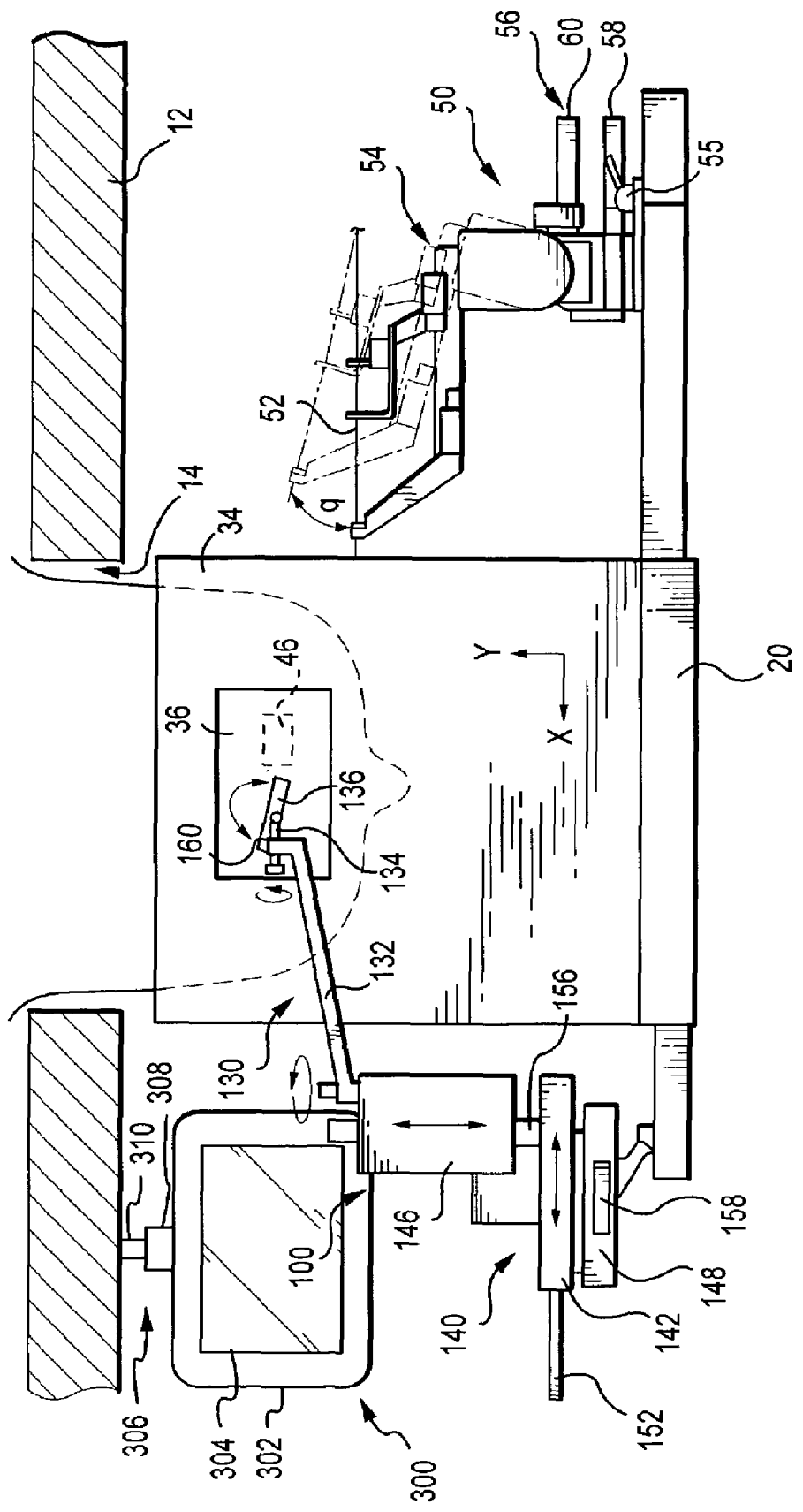
FIG. 2 is a partial end cross-sectional view of the embodiment of FIG. 1 cut along AA.

After the biopsy subassembly 50 is positioned as desired, biopsy procedures may be completed. In conjunction with such procedures, the ultrasound imaging head 110 may be utilized to provide continuous, successive depth profile images, thereby allowing for real-time monitoring and user control of the advancement of the punction instrument 52 into the breast. More particularly, when the punction instrument is positioned at an angle θ as illustrated in FIG. 2, ultrasound imaging head 110 may be similarly angled at θ (e.g., relative to horizontal) so as to yield real-time ultrasound depth-profile images of the layer into which punction instrument 52 is advanced. After biopsy procedures are completed, ultrasound imaging head 110 may be repositioned so as to allow for pressure application of a cold pack 120.

Figure 3:
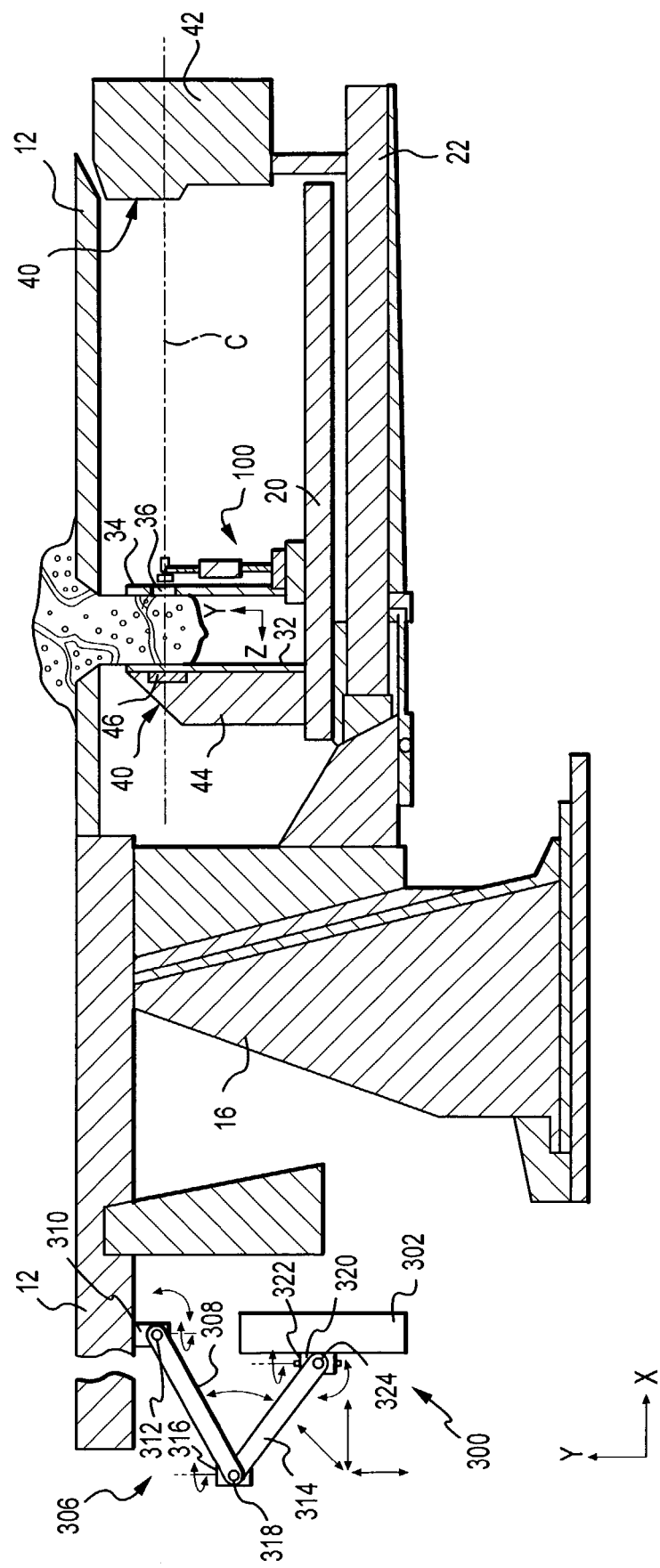
FIG. 3 is a partial side cross-sectional view of the embodiment of FIG. 1 cut along BB.
Figure 4:
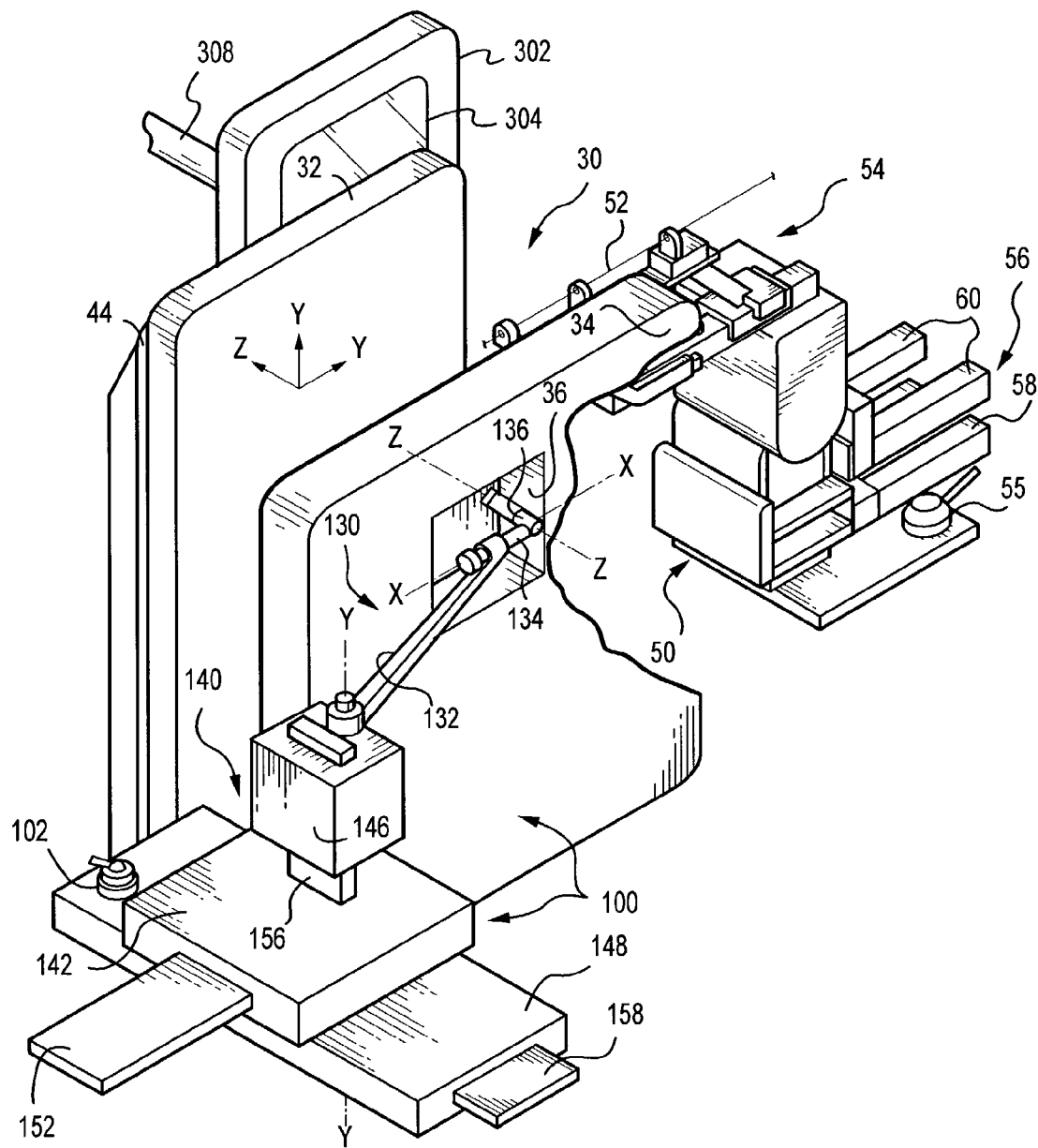
FIG. 4 is a perspective view of the immobilization, ultrasound imaging and biopsy assemblies of the embodiment of FIG. 1.

Referring to FIGS. 2-4, an ultrasound display system is generally identified by the reference numeral 300. In order to facilitate certain procedures such as a sampling of a suspicious lesion or tissue harvesting (or other targeted procedures such as guide wire placement, laser ablation or treatment delivery), it is desirable to provide an ultrasound display system in proximity to the patient's compressed breast. In this regard, the availability of a substantially real time ultrasound display is desirable to monitor the actual penetration path of a biopsy needle or other instrument into the patient's breast, for example, to verify that the instrument traverses the desired tissue and properly targets the area of interest. In the latter regard, it will be appreciated that certain instruments such as biopsy needles may have a tendency to deflect, particularly if the instrument contacts calcifications or other dense tissue structure. Accordingly, the availability of an ultrasound display system in proximity to the patient's breast allows the physician to verify that the instrument is properly targeting the area of interest and has not strayed due to deflection or otherwise. Moreover, the physician may wish to verify that a breast lesion has been sampled after activation of the biopsy instrument. Again, the availability of the ultrasound display system in proximity to the patient's breast facilitates such monitoring of a sampling process and sample verification.

In the illustrated embodiment, such monitoring is facilitated by providing an ultrasound display system 300 in proximity to the patient's breast under the table 12. In this regard, the system 300 may be mounted to the table 12, the pedestal 16 or another part of the support assembly 10, or may be otherwise positionable in proximity to the patient's breast beneath the table 12.

As noted above, the illustrated embodiment allows for sampling from various positions, including from either side of the patient's breast. In order to allow for convenient positioning of the ultrasound display system 300 for monitoring during a medical procedure, the illustrated system includes a support and positioning assembly 306. More specifically, the system includes a monitor 302 having a screen 304 for displaying ultrasound images. The illustrated assembly 306 allows for a three-dimensional translation of the monitor 302 as well as angular orientation of the screen 304 for easy viewing by a physician during such a medical procedure. The various types of motion that are accommodated by the assembly 306 are generally indicated by arrows in FIG. 3.

The support and positioning assembly 306 includes an articulated positioning system including an upper arm 308 and a lower arm 314. The upper arm is interconnected to the table 12 by way of a swivel mechanism 310 and an upper pin 312. The swivel mechanism 310 allows the assembly 306 to rotate relative to the Y axis as indicated in FIG. 3. In addition, the upper arm can pivot about upper pin 312. The upper arm 308 and lower arm 314 are interconnected in a manner that allows for relative swiveling and pivoting motion therebetween. In this regard, a central pivoting mechanism 316 allows for pivotal motion between the arms 308 and 314.

The lower arm 314 is also rotatable about pin 318 so as to allow for relative swiveling motion between arm 314 and arm 308. The lower arm 314 in turn is interconnected to the monitor 302 in a manner that allows for swiveling and pivoting motion therebetween. In this regard, lower pivoting mechanism 320 allows for pivotal motion between 314 and monitor 302. The monitor 302 can swivel relative to the arm 314 by rotating about lower pin 324. The lower pivoting mechanism 320 allows for rotation about the post 322. It will thus be appreciated that the assembly 306 allows for three-dimensional translation of the monitor to a position as desired by the physician/user, and also allows for positioning of the screen 304 in a desired angular orientation relative to both vertical and horizontal planes. It will be appreciated that other types of positioning mechanisms including slides, telescoping arms, and linear drive mechanisms can be used to provide some or all of the illustrated motions, and such motions may be actuated manually or driven by motors.

FIGS. 9A-9D show different ultrasound probe head configurations that may used to achieve different ultrasound signal characteristics in accordance with present invention. Referring first to FIG. 9A, a front perspective of an ultrasound head 900 in accordance with the present invention as shown. The illustrated head 900 is a linear head including a linear array of conventional ultrasound probe elements 902. Each such element includes an ultrasound transducer operative for both transmitting ultrasound signals to the patient and receiving echo signals returning from the patient. For example, the ultrasound elements may include a piezo transducer that is operative to transmit ultrasound signals by flexing or otherwise displacing in response to input electrical signals. Conversely, the return signals cause the transducer element to flex or otherwise displace thus creating an electrical output representative of the received return ultrasound signal. As is known, the wave form of the output signal provides information regarding the density of the tissue from which the signal was reflected. The transit time, i.e., the elapsed time between signal transmission and signal detection, provides information regarding the distance or depth relative to the head of the tissue that reflected the signal. In this manner, the ultrasound image provides information regarding the nature and location of tissue within the patient's breast. The illustrated head 900 may include, for example, 128 elements arranged in a single row and may be driven by, for example, a 10 MHz signal.

FIG. 9B shows a top schematic view of the probe 900. The probe head transmits a focused ultrasonic signal 901 having a profile as generally illustrated. In this regard, the signal includes a focal area within which high quality images can be obtained. In the illustrated embodiment, the depth of this focal region is indicated by $D_1$. In order to limit the ultrasound image to the area corresponding to depth $D_1$, the ultrasound imaging system may process the return signal over a corresponding time period. Specifically, ultrasound probes are generally operated in a series of alternating transmit and receive time periods. During a first transmit time period, an ultrasound signal is transmitted into the patient. At the end of the transmit time period, the transmission signal is terminated and the probe remains available for receiving return signals. The time at which return signals are received depends on the depth of the tissue from which such signals are reflected. Thus, an image corresponding to the area indicated by $D_1$ can be provided by processing the return signal over the corresponding time period.

FIG. 9C shows a front perspective view of a planar ultrasound probe head arrangement. The head 904 includes ultrasound elements arranged in rows 908 and columns 906. In use, the forward surface of the front column 908 is disposed approximate to the patient. Thus, the various columns 908 are disposed at varying distances from the patient.

FIG. 9D shows a top schematic view of the head 904 of FIG. 9C. The elements in each of the columns 908 transmit focused ultrasound signals 905. Because the columns are disposed at different distances from the patient or at different locations relative to the signal axis, the signals transmitted from the elements of the various columns 908 define a focal region having a depth $D_2$ that is greater than the depth $D_1$ of the head 900 of FIGS. 9A and 9B. The illustrated head 900 includes more than one column 908 and may include, for example, seven or more columns. Each column may include, for example, 128 elements 906.

In certain cases, the planar array configuration of head 904 provides imaging advantages. In this regard, it is desirable to provide a focal region depth, $D_2$, of at least about 5 centimeters as such depth allows for complete ultrasound imaging across the entire thickness of the compressed breast for most patients. The head 904 provides such focal depth. Accordingly, for most patients, the head 904 can provide high quality images of an area of interest within the patient's breast regardless of the location of the area of interest relative to the thickness of the patient's compressed breast.

Although the illustrated embodiment allows for utilization of x-ray images in conjunction with ultrasound images for three-dimensional localization of an area of interest within a patient's breast, it will be appreciated that such three-dimensional localization may be accomplished using only ultrasound imaging. For example, the ultrasound imaging assembly 100 may be initially used to obtain a scout image or image set. In this regard, arm 136 may be positioned so that the ultrasound head 116 is in a vertical orientation, i.e., substantially aligned with axis Y of FIG. 2. The assembly 100 can then be moved along the X axis of FIG. 2 so as to obtain ultrasound imaging exposures at various known locations along the X axis to thereby image the area of interest 46, e.g., in the form of multiple ultrasound image slices. In this manner, three-dimensional imaging information is provided for the location of interest 46 This information can then be used to provide targeting coordinates for the biopsy assembly 50.

During a subsequent medical procedure such as a needle biopsy, the arm 136 can be rotated such that it is aligned with axis 52 of a medical instrument such as a biopsy needle or gun. In this manner, the imaging assembly 100 can be used to provide substantially real time imaging information for monitoring insertion of the biopsy needle and sampling of the location of interest 46.

Figure 7:
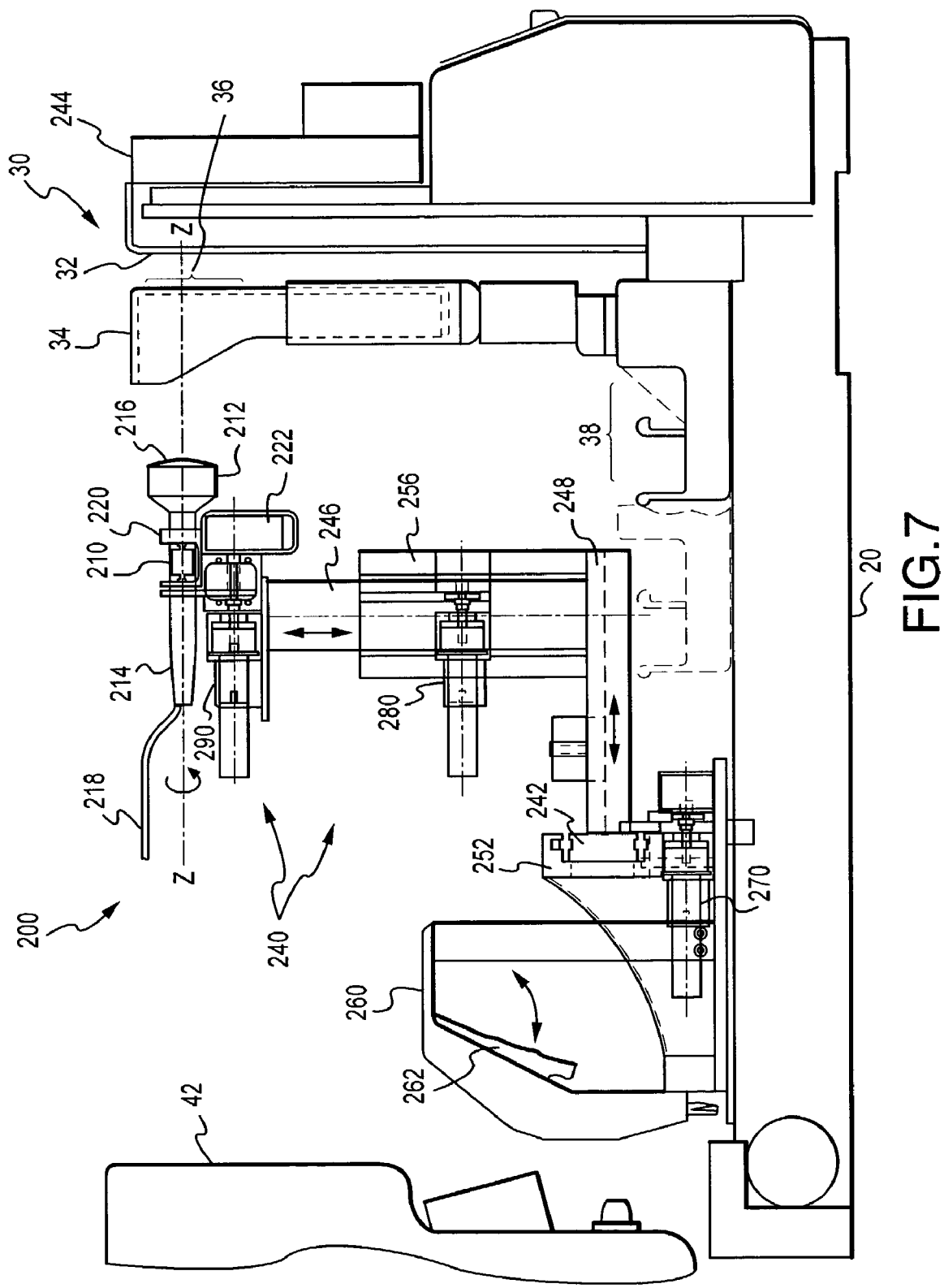
FIG. 7 illustrates a side-view of an alternative embodiment of an ultrasound imaging assembly comprising the present invention.
Figure 8:
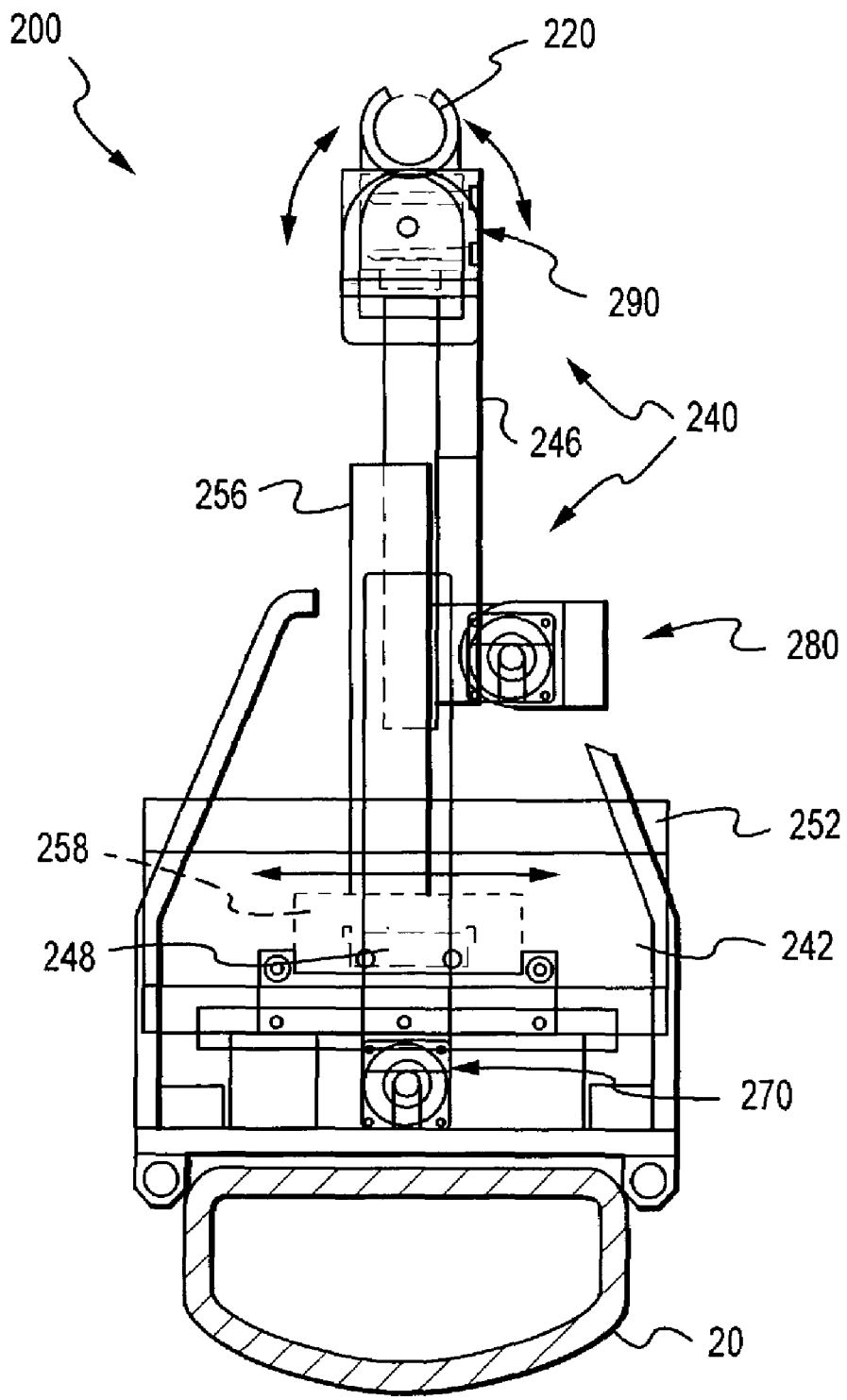
FIG. 8 illustrates a partially cut-away end view of the alternate ultrasound imaging assembly embodiment of FIG. 7.

FIGS. 7 and 8 pertain to an alternate embodiment of an ultrasound imaging assembly 200. In this regard, it should be noted that while the ultrasound imaging assembly 100 described hereinabove is supportably positioned below and on one side of a center axis of patient table 12, the alternate ultrasound imaging assembly 200 is provided to be supportably positioned immediately below and in substantial coaxial alignment with patient table 12. Such positioning of the ultrasound imaging assembly 200 allows for the alternate positioning of a biopsy a assembly 50, as described above, on either side below patient table 12, thereby yielding enhanced access to the above-noted predetermined XYZ frame of reference.

As illustrated in FIGS. 7 and 8, the ultrasound imaging assembly 200 is supportably positioned on and in coaxial relation to the first support arm 20. First support arm 20 also carries breast immobilization assembly 30. As with the embodiment described above, the breast immobilization assembly 30 includes a stationary face plate 32 and opposing compression paddle 34 for immobilizing a patient's breast therebetween. Compression paddle 34 again is x-ray transmittent and includes a window 36 for direct breast access therethrough by the ultrasound imaging assembly 200 and/or a biopsy assembly 50. Compression paddle 34 is selectively positionable along the first support arm 20. In this regard, a locking mechanism portion 38 of compression paddle 34 is sized in the embodiment of FIG. 7 for positioning under at least a portion of ultrasound imaging assembly 200 to yield overall enhanced access and compactness advantages.

Support arm 20 may also support an x-ray image receiver/imager 244 positioned in opposing relation to the x-ray tube source 42. Image receiver/imager 244 may comprise a removable radiographic film cassette and/or digital CCD camera assembly for partial or full-field, real time imaging. In the later regard, receiver/imager 244 may comprise a CCD assembly for full-field imaging as described in U.S. Pat. No. 5,526,394, hereby incorporated by reference.

With further respect to ultrasound imaging assembly 200, the assembly includes an ultrasound imaging probe 210 having an imaging head 212 (e.g., comprising an ultrasound transducer and/or linear array of transducers) positioned at the end of an elongated handle portion 214. The handle portion 214 is configured for selective grasping during hand-held use and alternatively for positioning within a holder 220 having a cradle-like configuration. In the illustrated embodiment, the holder 220 includes two interconnected and aligned u-shaped portions for conformally receiving a cylindrically shaped probe handle 214 (e.g., via "snap-in" and/or slide-in engagement). As will be appreciated, probe handle 214 and holder 220 may include projections and receiving slots or other means for establishing a predetermined positional relationship therebetween when engaged. The probe 210 may include an interconnect line 218 for transferring image data to a display/processor 60. For positioning relative to the predetermined XYZ frame of reference, holder 220 is mounted to an XYZ positioning assembly 240.

The XYZ ultrasound positioning assembly 240 includes X, Y and Z platforms 242, 246 and 248, respectively, mounted for selective, registered movement on corresponding support members 252, 256 and 258 relative to the predetermined XYZ frame of reference (i.e., defined between compression paddle 34 and face plate 32). The entire assembly 200 may be selectively removed from/interconnected to the support arm 20 utilizing a carrier assembly 260 having a depressible hand grasp 262 for retracting/advancing a locking pin(s) that interfaces with one or more openings along support arm 220.

Ultrasound imaging assembly 200 further comprises a first motor assembly 270 for driving X platform 242 for automated side-to-side movement of probe 210 in the X dimension. Similarly, ultrasound imaging assembly 200 also comprises a second motor assembly 280 for automated driving of platform 246 for up/down positioning of probe 210 in the Y dimension. Positioning in the Z dimension may be established by moving platform 248 relative to support member 258. Ultrasound imaging assembly 200 also includes a third motor assembly 290 for rotational movement of the holder 220, and in turn probe 210 mounted therewithin, about the axis ZZ. In this regard, holder 220 includes a microencoder for establishing the particular desired rotational angle of the ultrasound imaging probe head 212 (i.e., and the transducer and/or transducer array thereof) relative to the ZZ axis within the XY plane defined by the face 214 of the probe 210.

Figure 10:
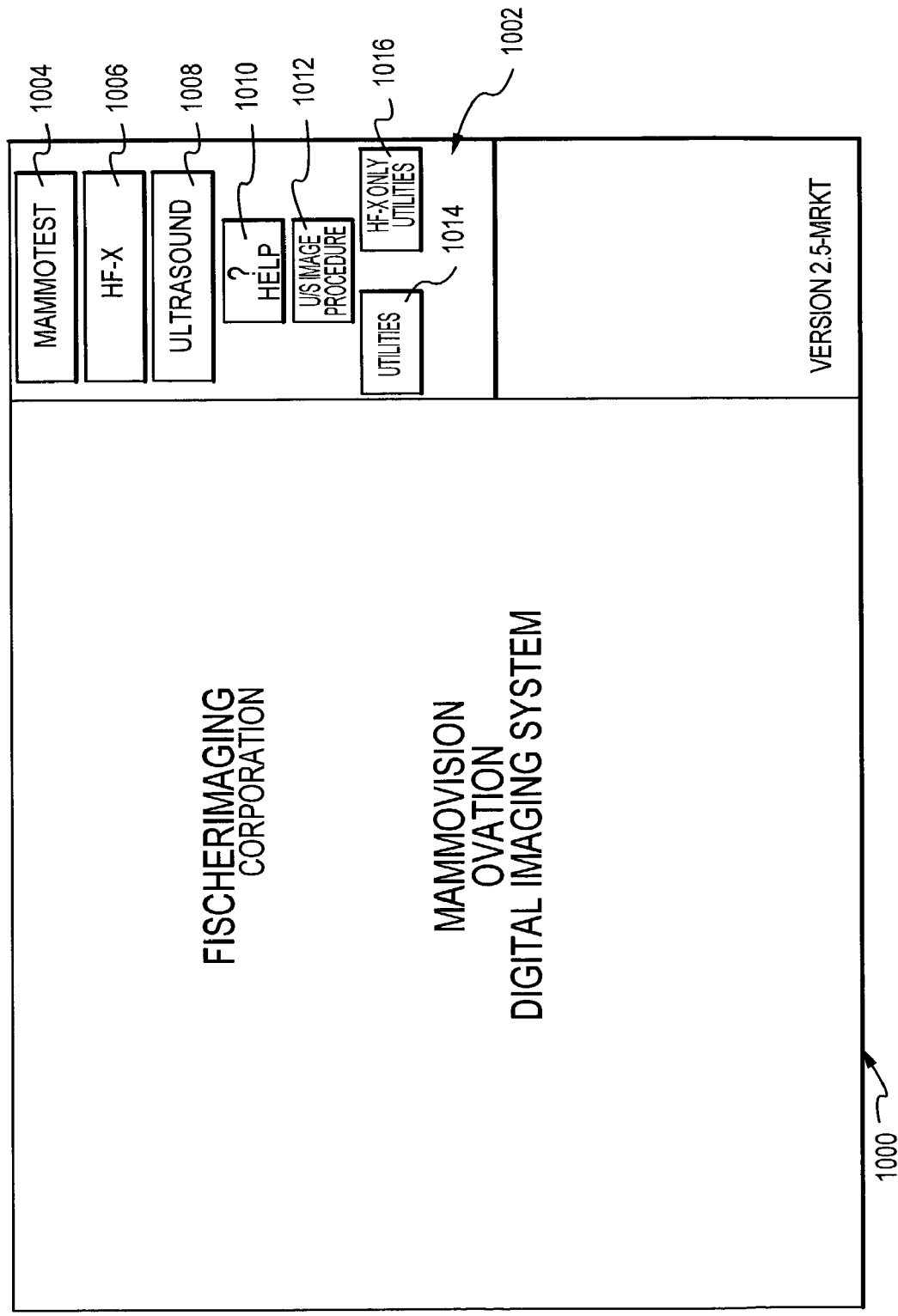

FIGS. 10-20 illustrate screens of a user interface system that may be employed in connection with the embodiments described above for procedures including localization, targeting and sampling of an area of interest in a patient's breast. Referring first to FIG. 10, an initial screen of the user interface system is shown. The screen may be displayed on a conventional display system such as an LCD or CRT computer monitor. For example, the screens may be displayed on the display/processor assembly 60 of FIGS. 1-6.

The initial screen, as shown in FIG. 10, includes an image display area 1000 and a user input area 1002. The user input area 1002 includes a number of graphical objects or buttons corresponding to particular functions such that the functions can be assessed and/or implemented by activating a cursor relative to the graphical objects, touching the graphical objects or other inputs relative to the objects. As shown in FIG. 10, the objects include a button 1004 labeled "Mammotest", a button 1006 labeled HF-X, a button 1008 labeled "Ultrasound", a button 1010 labeled "Help", a button 1012 labeled "U/S Image Procedure", a button 1014 labeled "Utilities" and a button 1016 labeled "HF-X Only Utilities". These buttons allow the user to select as between various operating modes of the system. In this regard, the system may be used for conventional upright x-ray procedures corresponding to the button HF-X, prone stereotactic imaging applications corresponding to the button labeled "Mammotest" or, of particular relevance with respect to the present discussion, for ultrasound-based procedures corresponding to the buttons 1008 and 1012.

The Help button 1010 can be used to access a variety of instructional information and operating information for the system. The Utilities button 1014 can be used to access various utilities screens, for example, relating to accessing records, changing display parameters such as brightness, etc. The HF-X Only Utilities button 1016 provides access to utility information relating to the HF-X mode of operation. For the purposes of the present discussion, the user may activate ultrasound button 1008 in order to initiate ultrasound related procedure.

FIG. 11 illustrates a subsequent screen of the user interface system. The screen includes a display area 1102, a user input area 1104 and an instruction area 1106. The instruction area 1106 provides instructions to the user with regard to the current screen. In this regard, the illustrated screen includes instructions directing the user to enter patient data and to click "Done" when finished. The user may then enter a patient name, patient identification number, a physician name, a date of procedure, a technician's initials and any other information as desired into the display area 1102. Such information is used, for example, for purposes of maintaining records and facilitating later retrieval of desired images.

The user input area includes graphical objects 1108, 1110 and 1112 respectively labeled "Lateral Approach", "Target on Scout", and print DB Entry. The Print button 1112 can be used to provide a hard copy of the screen including, for example, the entered patient information. The lateral approach button 1108 allows the user to indicate when a lateral approach is being utilized for imaging the patient's breast. The Target on Scout 1110 allows the user to indicate that a scout image is to be obtained. For example, an x-ray scout image may initially be displayed to identify the area of interest for use in positioning the targeted ultrasound system. It will thus be appreciated that the sequence of screens presented to the user may vary depending on the specific procedure to be implemented as indicated through appropriate entries relative to the displayed graphical objects.

Figure 12:
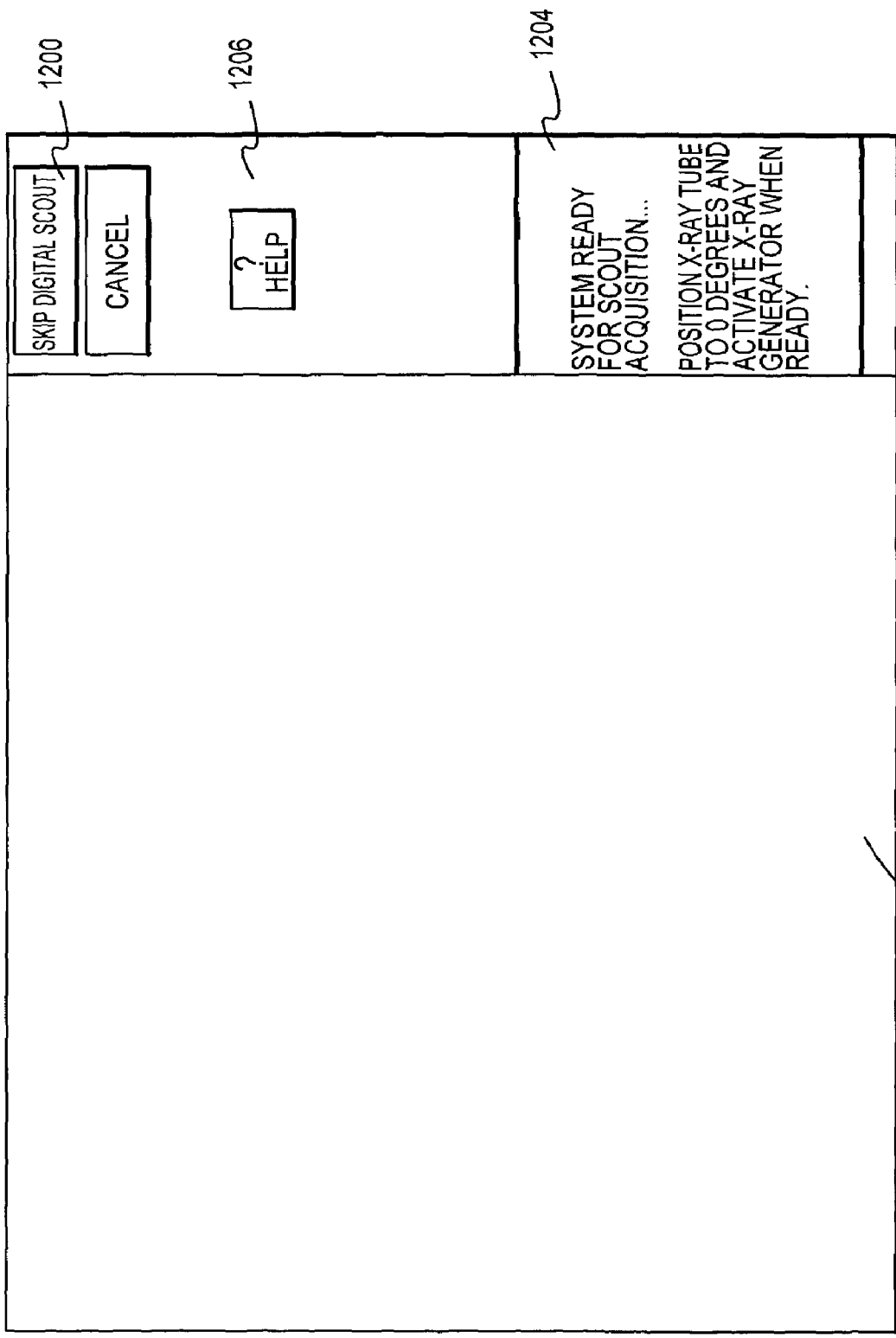

FIG. 12 illustrates a screen which may be presented in the case where the user desires to obtain an initial scout image. As shown, the display area 1202 is blank pending acquisition of the scout image. The instructions in area 1204 indicate that the system is ready for acquiring the scout image and provides information regarding positioning of the x-ray tube. Specifically, the instructions indicate that the x-ray tube should be positioned to 0 degrees corresponding to a top to bottom imaging angle relative to the patient's breast. It is also possible for the user to skip the digital scout image by selecting the skip digital scout button 1208 in input area 1206. For acquisition of the scout image, the ultrasound imaging system may be removed to avoid interference.

Figure 13:
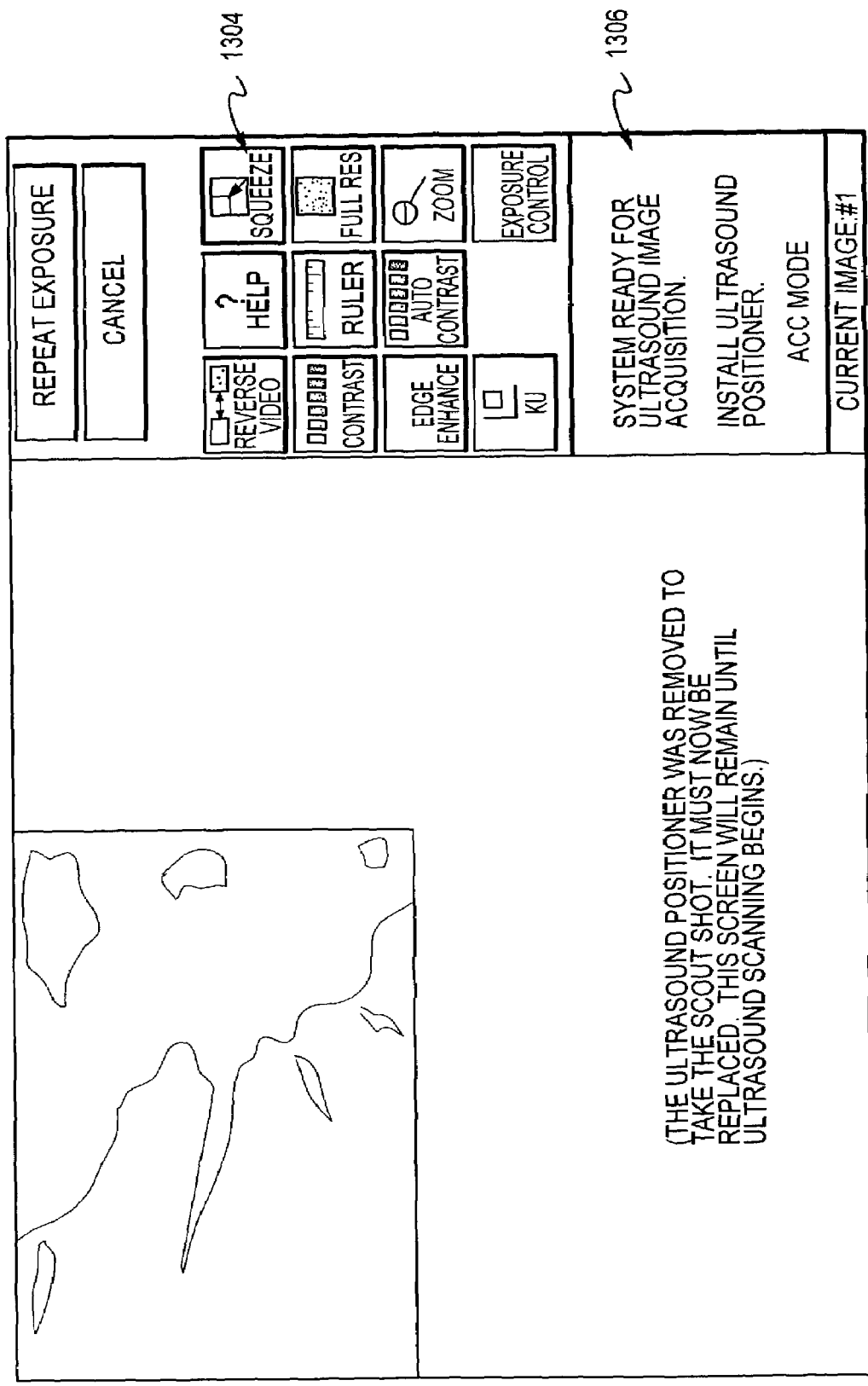

As noted above, the three-dimensional coordinates of a location of interest within the patient's breast can be identified based on a digital x-ray image and an ultrasound image. In FIG. 13, a digital x-ray image is displayed in the display area 1302. This x-ray image can be used to identify the location of interest relative to the two dimensional image so as to allow for appropriate positioning of the ultrasound imaging system.

In order to enhance the image and facilitate identification of the location of interest, a number of image enhancement features can be accessed and implemented relative to the buttons provided in user input area 1304. These buttons include: a reverse video button for reversing the tone of the displayed x-ray image, i.e., to provide a negative of the displayed image; a squeeze button for minimizing the display area occupied by the image; a contrast button for varying the contrast of the image; a ruler button for providing a scale for dimensional reference with respect to the image; a fall resolution button for displaying the image with maximum resolution; an edge enhancement button for identifying and enhancing the edges of displayed structural features for enhanced structure identification; an autocontrast button for automatically fixing the contrast level; a zoom button for zooming in on a particular area of the image, for example, as identified by a cursor input; a KV button for activating a kilovolt sensor to control the power of an exposure; and an exposure control button for allowing the user to manually control exposure. After the image has been displayed to the satisfaction of the user, the user may proceed to ultrasound image acquisition. In this regard, the instruction box 1306 provides instructions to install the ultrasound positioner (an ultrasound imaging system).

Figure 14:
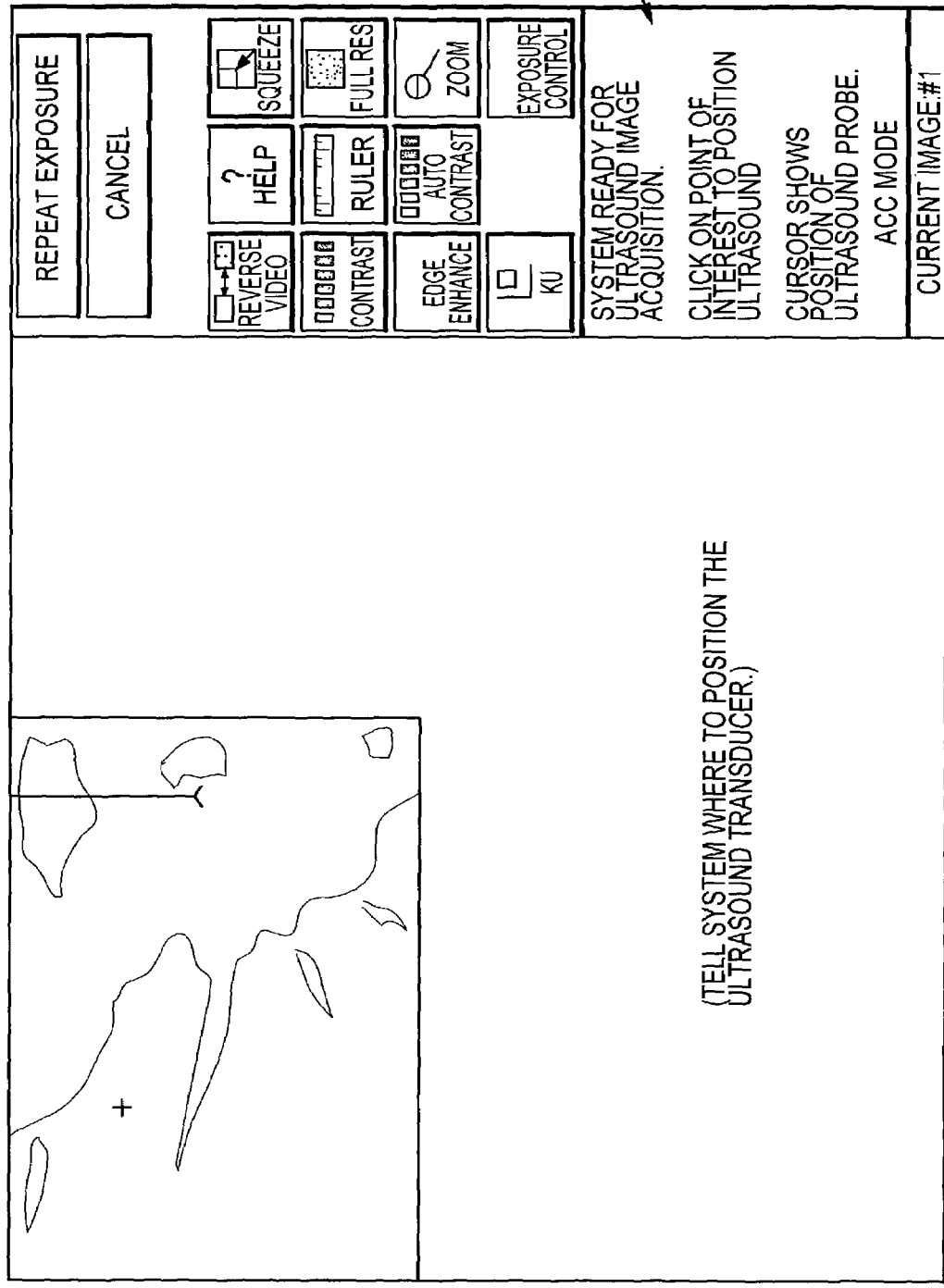
Figure 15:
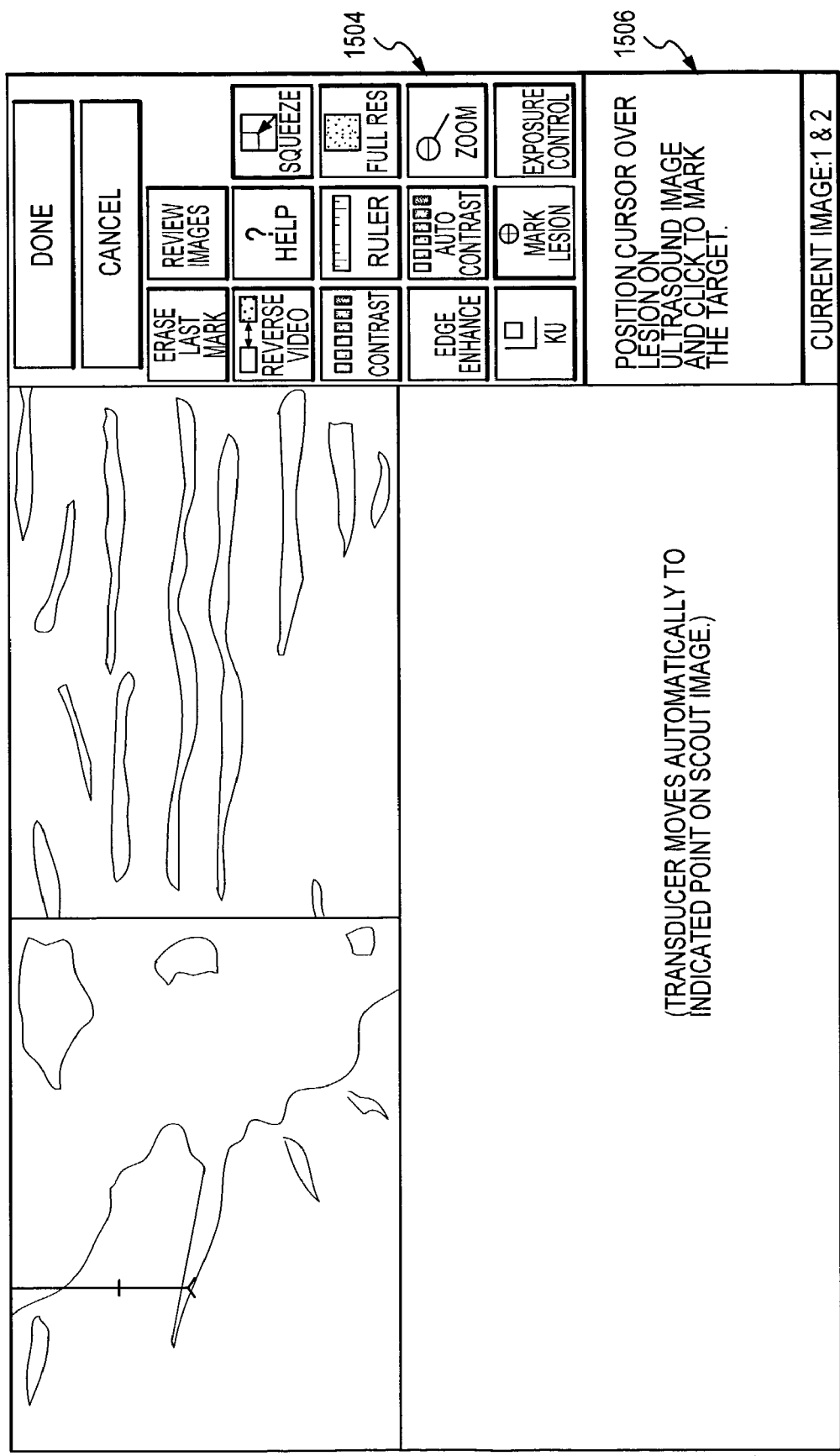

FIGS. 14 and 15 illustrate a process for positioning an ultrasound probe. In the illustrated implementation of the present invention, the x-ray image is used in conjunction with an ultrasound image to localize an area of interest in three dimensions in the following manner. First, the x-ray image is display in the display area as shown at 1402 in FIG. 14. A line within the image in the display area 1402 indicates a current position of the ultrasound probe. For convenient reference, an arrowhead is provided at one end of the line to indicate a rearward end of the ultrasound probe. As indicated by the instructions in area 1404, the user can position the ultrasound probe by clicking on the location of interest in the x-ray image. In response to this data entry, the motors associated with the ultrasound positioner will drive the ultrasound probe to the desired location relative to the two dimensions of the x-ray image.

As indicated in FIG. 15, the ultrasound probe automatically moves to the indicated point on the x-ray scout image. It will thus be appreciated that two dimensional coordinates of the location of interest are encoded into the position of the ultrasound transducer. The ultrasound imaging system can then be used to identify the third dimension, or depth, of the location of interest. To this end, the ultrasound image system is activated to provide a second image which is displayed in the display area 1502 as shown in FIG. 15. In order to identify the location of interest relative to the ultrasound image, the user first selects the mark lesion button in user input area 1504 and then positions and activates the cursor over the location of interest on the ultrasound image, per the instructions in area 1506. This process is illustrated in FIG. 16.

Figure 16:
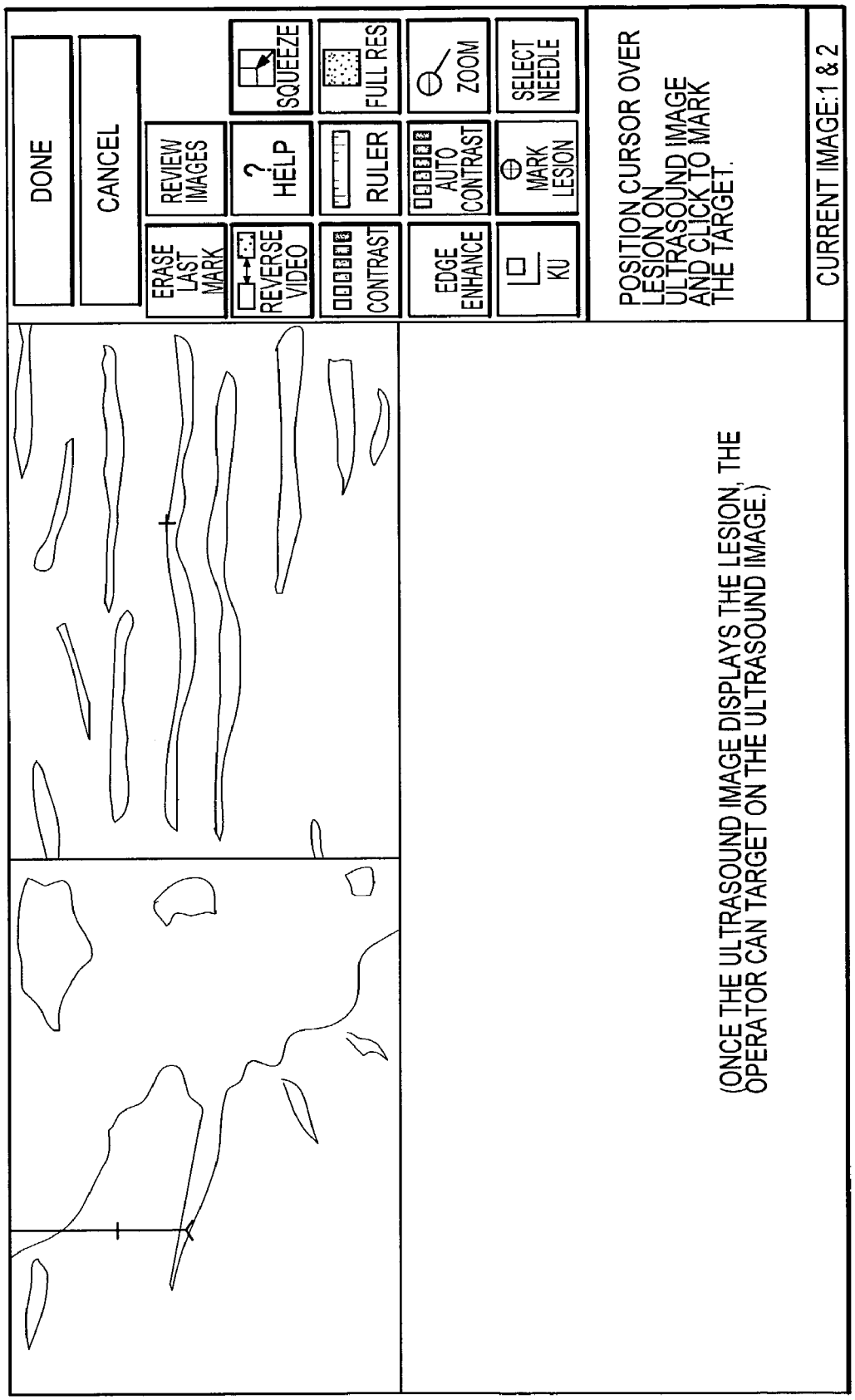

FIGS. 15 and 16 also include a select needle button in the user input area. It will be appreciated that different biopsy needles have different dimensions which need to be accounted for in targeting the location of interest for sampling. Such information can be entered by using the select needle button. In addition, it is possible in accordance with the present invention to show a representation of a needle on the images, for example, to project the penetration path so that a physician can plan a sampling procedure. For example, a physician may wish to alter a potential penetration path in order to traverse less breast tissue or to avoid certain intervening structure on the way to the location of interest.

Figure 17:
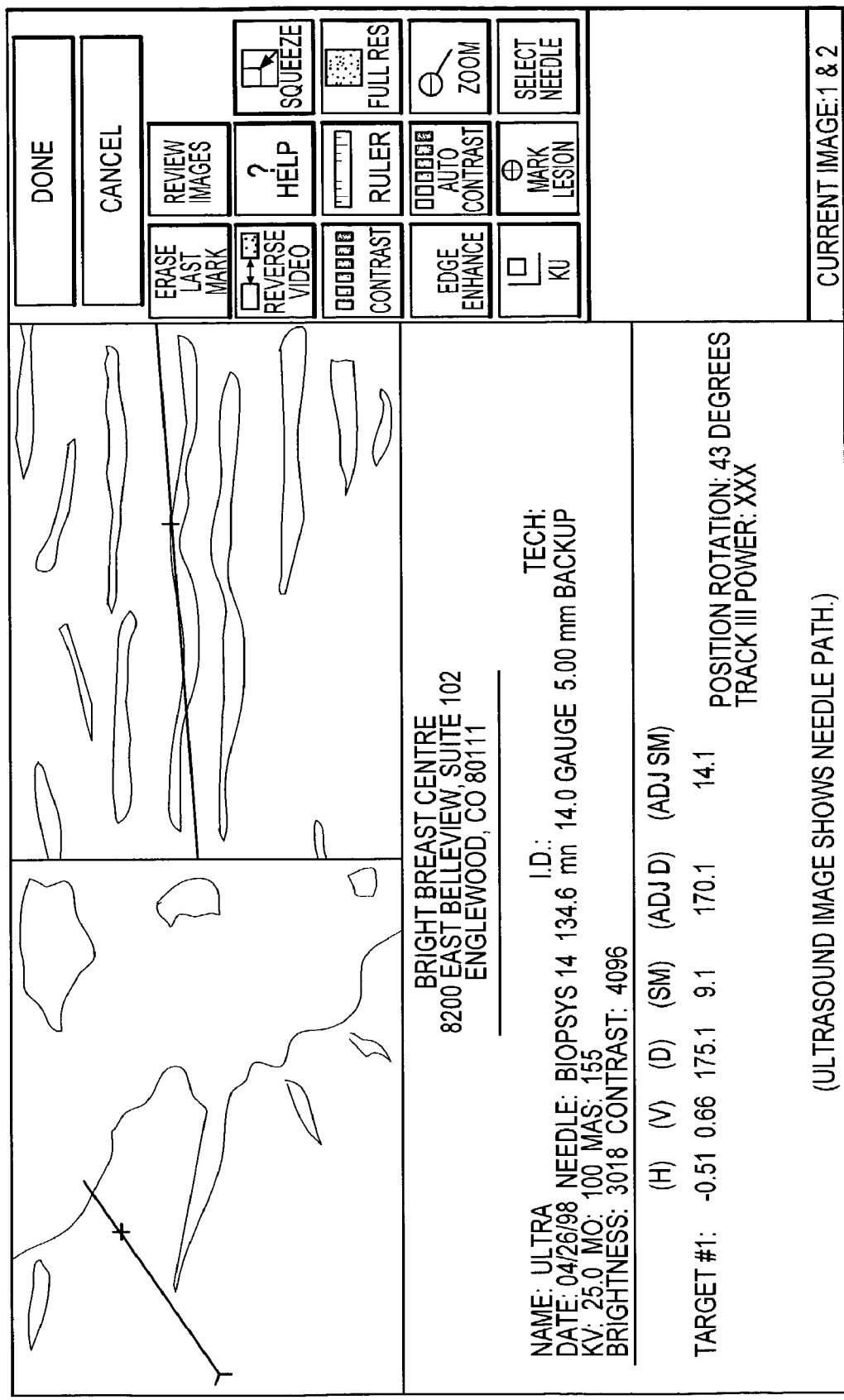

FIG. 17 shows the results of a three dimensional localization procedure. Specifically, the target coordinates together with certain other patient and procedural information are displayed in display area 1702. The information displayed in this regard may include three-dimensional coordinate information as well as adjusted coordinate information to account for certain offsets relating, for example, to the geometry of the needle holder and needle. Also shown in the ultrasound image in the display area 1702 is a projected needle path for the sampling procedure. In order to further enhance the physician's ability to understand the displayed images, an indication may be provided in the display area 1702 or otherwise regarding the angular orientation of the displayed images. In this regard, the illustrated display area 1702 includes an indication that the ultrasound positioner is rotated to a position identified as 43 degrees.

Figure 18:
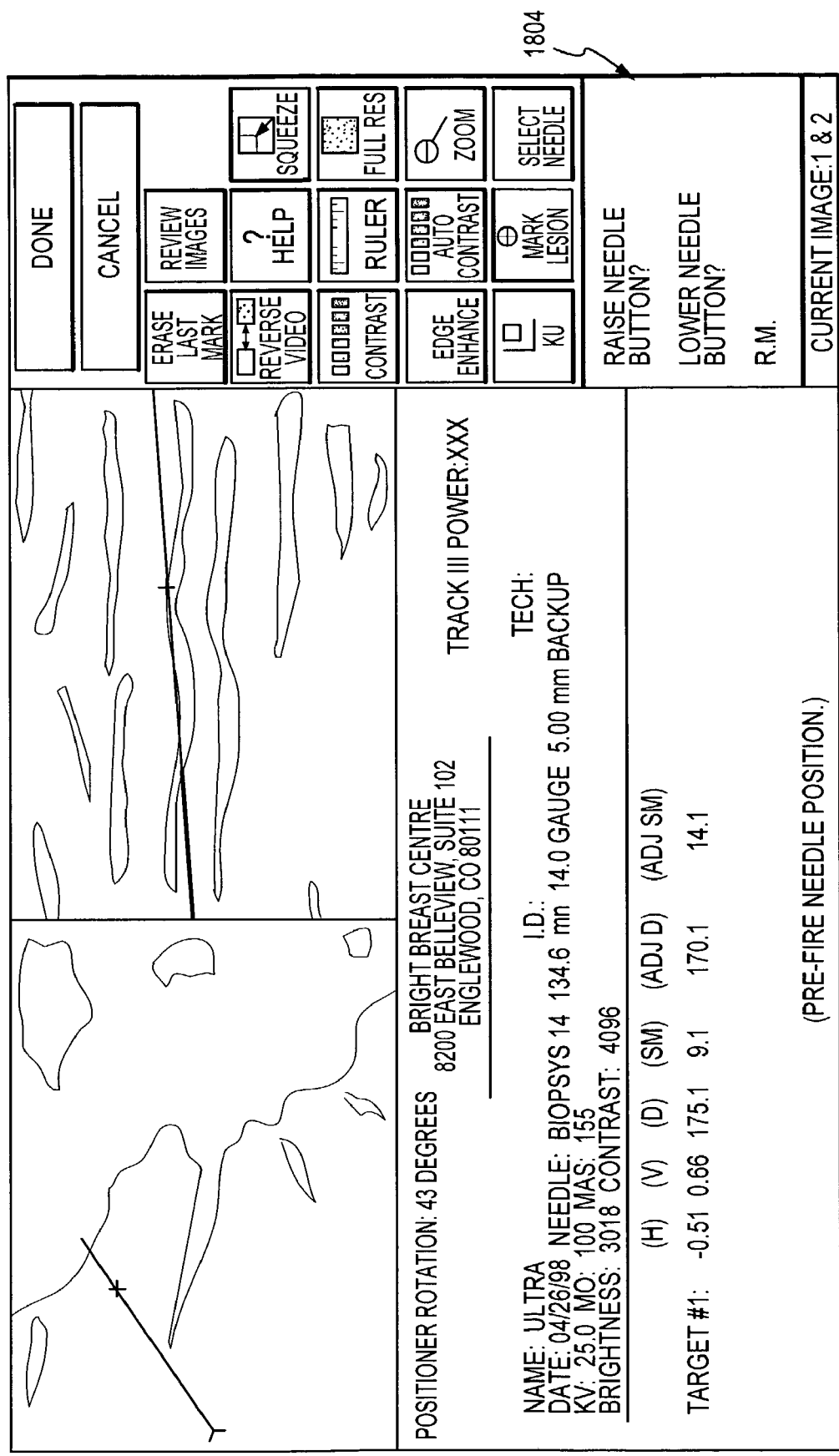
Figure 19:
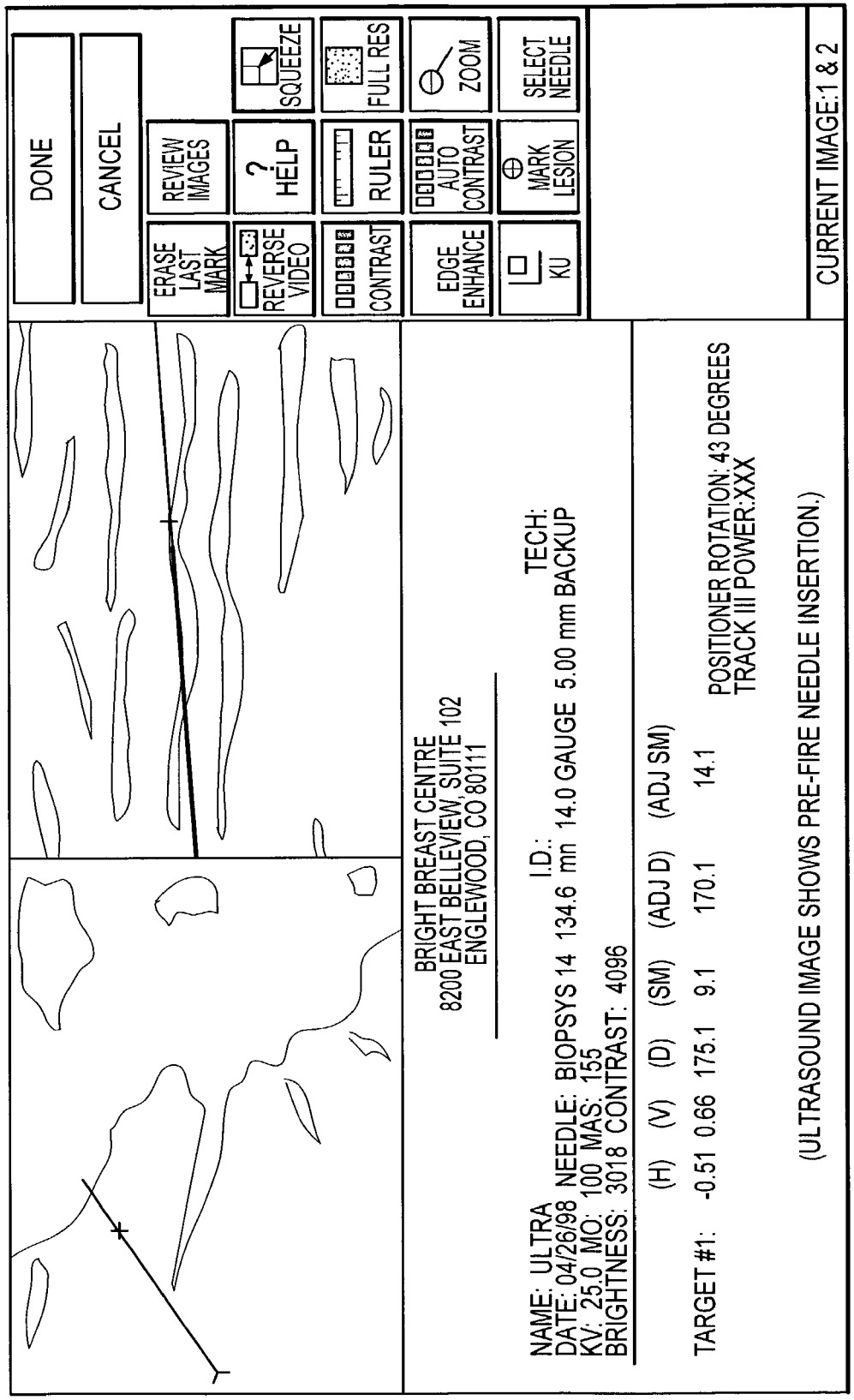
Figure 20:
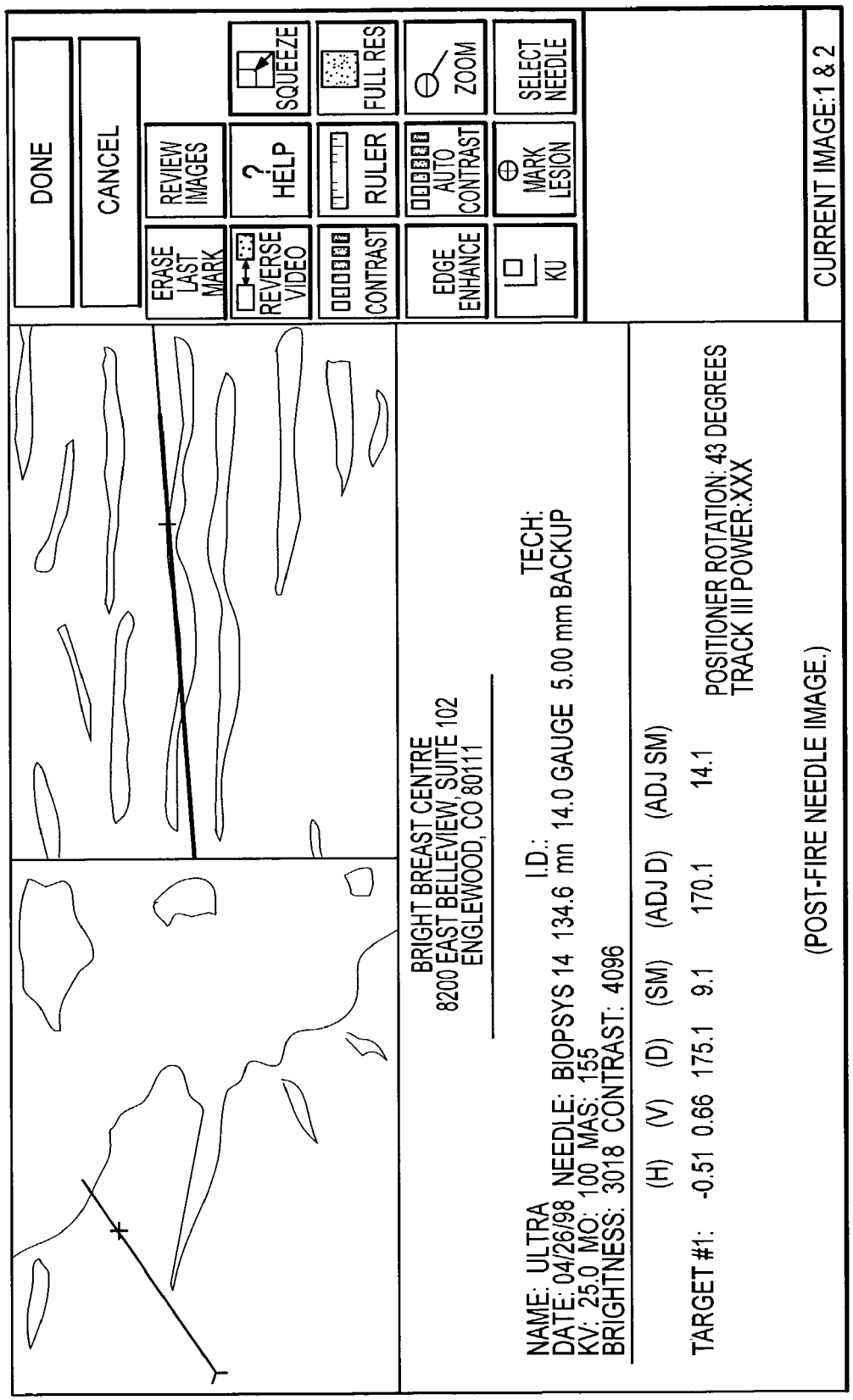

FIGS. 18-20 illustrate a subsequent needle biopsy procedure. As has been described above, the ultrasound probe may be aligned relative to the penetration axis of the biopsy needle such that penetration of the biopsy needle can be viewed in real time. This video information, which is also displayed on the under table monitor, is shown in FIGS. 18-20. Specifically, FIG. 18 shown an initial penetration of the biopsy needle towards the location of interest. An indicated of the penetration path is overlaid in the image relative to the biopsy needle. The biopsy needle may deflect from its intended course, for example, due to contact with calcifications or other dense structure within the patients breast. For this reason, the availability of real time ultrasound imaging during this process is an important advantage of the illustrated system. In the event that the needle appears to be diverting from the intended course, the user can manually correct the positioning of the biopsy needle. In this regard, the instructions in area 1804 remind the user to consider correcting the course by using raised needle and lower needle buttons provided in conjunction with the ultrasound probe positioner. If desired, the illustrated system can be programmed to identify any diversion between the actual penetration path and the projected penetration path so as to issue an alert or allow for automatic correction.

FIG. 19 shows a position of the biopsy needle prior to activation of the needle to harvest tissue or cells from the area of interest. In this regard, typical biopsy needle guns are operated by positioning the biopsy needle a short distance from the location of interest and pointed towards the location of interest and then activating the gun so that the needle is thrown a distance through the area of interest such as under spring force. In this regard, FIG. 19 shows the pre-fire position of the biopsy needle and FIG. 20 shows the post-fire position of the biopsy needle. These images can be viewed in real time so that the physician may be satisfied that the location of interest has in fact been sampled and that the resulting biopsy will be reliable.

While the present invention has been described in relation to one embodiment, it will be appreciated that the invention may be utilized in numerous additional embodiments and procedures. Such additional embodiments and procedures are within the scope of the present invention, as defined by the claims which follow.

What is claimed is:

1. A method comprising:
   immobilizing a patient's breast using a selected immobilization assembly;

imaging the immobilized breast with penetrating radiation to obtain at least one two-dimensional penetrating radiation image of the breast;

displaying the at least one penetrating radiation image of the breast and deriving therefrom first spatial information regarding a region of interest in the breast;

positioning an ultrasound image display screen in close proximity to the immobilized breast by moving the screen using an articulating supporting structure;

carrying out ultrasound imaging of the immobilized breast to obtain ultrasound images of the breast substantially in real time and deriving therefrom second spatial information regarding the region of interest;

displaying said ultrasound images on said ultrasound display screen substantially in real time and in spatial correlation; and using said displayed ultrasound images and said first and second information regarding the region of interest to guide an insertion of a medical instrument in the immobilized breast including by operatively interconnecting a processor with at least the immobilization assembly and the medical instrument, wherein said processor controls the relative positions thereof to position the medical instrument relative to said region of interest.

2. A method as in claim 1 in which said moving comprises moving the ultrasound image display screen in a motion having at least four degrees of freedom.

3. A method as in claim 2 in which said degrees of freedom include three-dimensional translation and angular motion.

4. A method as in claim 1 including displaying said at least one penetrating radiation image at a penetrating radiation image display screen that is separate from said ultrasound image display screen.

5. A method as in claim 1 in which said ultrasound images provide three-dimensional information regarding the region of interest in the breast for needle biopsy of said region.

6. A method as in claim 1 in which said at least one penetrating radiation image of the breast provides two-dimensional information regarding the region of interest in the breast and said ultrasound images provide spatial information regarding at least a third dimension regarding the region of interest.

7. A method as in claim 1 including providing a computer with third spatial information regarding the region of interest derived from said first and second spatial information, and calculating fourth spatial information regarding a path of a medical instrument for penetrating the immobilized breast.

8. A method as in claim 7 including providing the computer with needle information regarding parameters of a biopsy needle and using the needle information in calculating said path.

9. A method comprising:

immobilizing a patient's breast;

imaging the immobilized breast with penetrating radiation to obtain at least one two-dimensional penetrating radiation image of the breast;

displaying the at least one penetrating radiation image of the breast and deriving therefrom first spatial information regarding a region of interest in the breast;

positioning an ultrasound image display screen in close proximity to the immobilized breast by moving the screen using an articulated supporting structure;

carrying out ultrasound imaging of the immobilized breast to obtain ultrasound images of the breast substantially in real time and deriving therefrom second spatial information regarding the region of interest;

displaying said ultrasound images on said ultrasound image display screen substantially in real time; and using displayed ultrasound images regarding the region as displayed on the ultrasound image display screen to monitor an insertion of a medical instrument in the immobilized breast;

wherein said ultrasonic imaging comprises using an ultrasound probe that automatically moves to a selected position in response to the selection of a region of interest in said penetrating radiation image.

10. A method as in claim 9 in which said ultrasound imaging includes scanning the breast with ultrasound beams.

11. A method as in claim 9 in which said ultrasound imaging includes acoustically coupling ultrasound transducer with the immobilized breast through an opening in a breast immobilizing structure.

12. A method as in claim 9 including using a motorized structure and information from the penetrating radiation images to automatically position ultrasound transducers relative to the region of interest in the breast.

13. A method as in claim 12 including scanning at least the region of the interest with ultrasound beams from said transducers.

14. A method as in claim 9 including providing a computer with needle information regarding parameters of a biopsy needle, and using the needle information in calculating a breast penetration path for said medical instrument.

15. A system comprising:

a breast immobilizing structure for securing a patient's breast in a selected position;

a penetrating radiation imager selectively imaging the immobilized breast with penetrating radiation to obtain penetrating radiation images of the breast;

an ultrasound imager having a display screen and an articulated support structure for selectively positioning the screen in close proximity to the immobilized breast;

said ultrasound imager selectively carrying out ultrasound imaging of the immobilized breast and thereby obtaining ultrasound images of the breast substantially in real time;

an image display and a computer coupled with the penetrating radiation imager to receive said images therefrom, with the ultrasound imager to receive said ultrasound images therefrom, and with the display to selectively display the penetrating radiation images and the ultrasound images, and configured to process the images and user inputs to derive spatial information regarding a region of interest in the immobilized breast; and a medical device for insertion into a patient and a controller operatively connected with the computer and with the medical device and using said displayed ultrasound images and said spatial information regarding the region of interest to automate guidance of an insertion of the medical device in the immobilized breast.

16. A system as in claim 15 in which said image display comprises a first graphical display displaying one or more of the penetrating radiation images of the patient's breast for identification of the region of interest within the patient's immobilized breast;

a users interface operatively associated with said first graphical display, far entering a selection by a user of a portion of at least one of said displayed penetrating radiation images wherein said portion is associated with said identified region of interest; and a second graphical display, separate from said first graphical display and located proximate to the patient's immobilized breast, for providing substantially real-time images responsive to said selection by said user, in connection with said first display, of said selected portion of said patient's immobilized breast so that the user can monitor insertion of said medical device to said identified region of interest within said patient's immobilized breast using said second graphical display located proximate to said patient's immobilized breast.

17. A system as in claim 15 in which said second graphical display is movable relative to said immobilizer such that a user can locate said second graphical display for convenient viewing during insertion of said medical device into said identified region of interest within said patient's immobilized breast.

18. A system as in claim 15 in which said second graphical display is angularly moveable so that a user can adjust an angle of said graphical display for convenient viewing during insertion of said medical device to said identified region of interest within said patient's immobilized breast.

19. A system as in claim 15 in which said ultrasound images comprises ultrasound transducers and a supporting structure for selectively positioning the transducers in acoustic coupling with the immobilized breast, and including position indicators providing information regarding the spatial position of the transducers relative to a frame of reference related to said penetrating radiation imaging and ultrasound imaging.

* * * * *